US011270781B2

(12) United States Patent
Struble et al.

(10) Patent No.: US 11,270,781 B2
(45) Date of Patent: *Mar. 8, 2022

(54) STATISTICAL ANALYSIS FOR NON-INVASIVE SEX CHROMOSOME ANEUPLOIDY DETERMINATION

(71) Applicant: Ariosa Diagnostics, Inc., San Jose, CA (US)

(72) Inventors: Craig Struble, San Jose, CA (US); Arnold Oliphant, San Jose, CA (US); Eric Wang, San Jose, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 1151 days.

This patent is subject to a terminal disclaimer.

(21) Appl. No.: 13/917,329

(22) Filed: Jun. 13, 2013

(65) Prior Publication Data

US 2013/0275103 A1 Oct. 17, 2013

Related U.S. Application Data

(63) Continuation-in-part of application No. 13/790,642, filed on Mar. 8, 2013, now Pat. No. 9,994,897, and a continuation-in-part of application No. 13/338,963, filed on Dec. 28, 2011, now Pat. No. 8,700,338, which is a continuation-in-part of application No. 13/316,154, filed on Dec. 9, 2011, now abandoned.

(60) Provisional application No. 61/436,135, filed on Jan. 25, 2011.

(51) Int. Cl.

| G16B 5/20 | (2019.01) |
| G16B 5/00 | (2019.01) |
| G16B 20/00 | (2019.01) |
| G16B 20/10 | (2019.01) |
| G16B 20/20 | (2019.01) |
| G16B 40/00 | (2019.01) |

(52) U.S. Cl.
CPC ............... *G16B 5/20* (2019.02); *G16B 5/00* (2019.02); *G16B 20/00* (2019.02); *G16B 20/10* (2019.02); *G16B 20/20* (2019.02); *G16B 40/00* (2019.02)

(58) Field of Classification Search
None
See application file for complete search history.

(56) References Cited

U.S. PATENT DOCUMENTS

| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,136,229 A | 10/2000 | Cui et al. |
| 6,141,096 A | 10/2000 | Stern et al. |

(Continued)

FOREIGN PATENT DOCUMENTS

| CN | 103074416 A | 5/2013 |
| GB | 2299166 | 9/1996 |

(Continued)

OTHER PUBLICATIONS

Wiedmann et al. Ligase Chain Reaction (LCR)—Overview and Applications Genome Research vol. 3, pp. S51-S64 (Year: 1994).*
Wright et al. The use of cell-free fetal nucleic acids in maternal blood for non-invasive prenatal diagnosis Human Reproduction Update vol. 15, pp. 139-151 (Year: 2009).*
Yi et al. A New Genotyping Method for Detecting Low Abundance Single Nucleotide Mutations Based on Gap Ligase Chain Reaction and Quantitative PCR Assay Cellular Biochemistry and Biophysics vol. 62, pp. 161-167 (Year: 2012).*
Zimmermann et al. Noninvasive prenatal aneuploidy testing of chromosomes 13, 18, 21, X, and Y, using targeted sequencing of polymorphic loci. Prenatal Diagnosis vol. 32, pp. 1233-1241 (Year: 2012).*

(Continued)

*Primary Examiner* — John S Brusca
(74) *Attorney, Agent, or Firm* — Mintz Levin Cohn Ferris Glovsky and Popeo, P.C.

(57) ABSTRACT

The present invention provides methods for non-invasive determination of X and/or Y chromosomal abnormalities indicative of aneuploidy or sex mosaicisms in a maternal sample by detecting and determining the relative contribution of genetic sequences from the X chromosome and/or the Y chromosome in the maternal sample.

32 Claims, 9 Drawing Sheets

(56) References Cited

U.S. PATENT DOCUMENTS

| | | |
|---|---|---|
| 6,156,504 A | 12/2000 | Goeke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Lo et al. |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,293,076 B2 | 10/2012 | Fan et al. |
| 8,318,430 B2 | 11/2012 | Chuu et al. |
| 2002/0045176 A1 | 4/2002 | Lo et al. |
| 2002/0132241 A1 | 9/2002 | Fan et al. |
| 2003/0003459 A1 | 1/2003 | Stahl |
| 2003/0044388 A1 | 3/2003 | Lo et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsui et al. |
| 2005/0191656 A1 | 9/2005 | Drmanac et al. |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0096766 A1 | 4/2008 | Lee |
| 2008/0138809 A1 | 6/2008 | Kapur et al. |
| 2008/0206749 A1 | 8/2008 | Lo et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan et al. |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0039724 A1 | 2/2012 | Rossi et al. |
| 2012/0100548 A1 | 4/2012 | Rava et al. |
| 2012/0108460 A1 | 5/2012 | Quake et al. |

(56) References Cited

U.S. PATENT DOCUMENTS

| | | |
|---|---|---|
| 2012/0165203 A1 | 6/2012 | Quake et al. |
| 2012/0184449 A1 | 6/2012 | Hixson |
| 2012/0191358 A1 | 7/2012 | Oliphant et al. |
| 2012/0191359 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0230258 A1 | 9/2012 | Miki et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava |

FOREIGN PATENT DOCUMENTS

| | | |
|---|---|---|
| GB | 97044 | 3/1998 |
| JP | 2016-526377 A | 9/2016 |
| WO | WO87/006270 | 10/1987 |
| WO | WO90/06995 | 6/1990 |
| WO | WO99/47964 | 9/1999 |
| WO | WO2003/038120 | 5/2003 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO2011/090556 | 1/2010 |
| WO | WO2011/090557 | 1/2010 |
| WO | WO2011/090558 | 1/2010 |
| WO | WO-2013/000100 A1 | 1/2013 |
| WO | WO-2014/200579 A1 | 12/2014 |

OTHER PUBLICATIONS

Search Report dated Aug. 12, 2014 for PCT/US2013/75683, entire document.
Abadia-Molina, et al., "Immune phenotype and cytotoxic activity of lymploycytes from human term decidua against trophoblast", J. of Reproductive Immunology, n31:109-23 (1996).
Agostini, et al., "Circulating cell-free DNA: a promising marker of pathologic tumor response in rectal cancer patients receiving preoperative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (2003).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63(1979).
Ashoor, et al., Fetal Fraction in Maternal Plasma Cell-Free DNA at 11-13 Weeks Gestation: Effect of Maternal and Fetal Factors, Fetal Dian Ther DOI:10.1159/000337373 (Pub'd online May 4, 2012), entire document.
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029, entire document.
Arnheim et al., "Molecular evidence for genetic exchanges among ribosomal genes on nonhomologous chromosomes in man and apes", PNAS USA, 77(12):7323-27 (1980).
Bandyopadhyay, et al, "Identification and characterization of satellite III subfamilies to the acrocentric chromosomes", Chromosome Research, 9:223-33 (2001).
Batzer and Deininger, "ALU Repeats and Human Genomic Diversity", Nature, 3:370-79 (2002).

Beard, "Embryological Aspects and Etiology of Carcinoma", The Lancet, Jun. 21, 1902, pp. 1758-1761.
Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986, pp. 506-509.
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Bradstock, et al., "Functional and phenotypic assessment of neonatal human leucocytes expressing natural killer cell-associated antigen", Immunology and Cell Biology, 71:535-42 (1993).
Camaschella, et al., "Prenatal Diagnosis of Fetal Hemoglobin Lepore-Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Natl Cancer Inst., 97(9):643-55 (2005).
Cicuttini and Boyd, "Hemopoietic and Lymphoid Progenitro Cells in Human Umbilical Cord Blood", Developmental Immunology, 4:1-11 (1994).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011), entire document.
Chim, et al., "Detection of the placental epigenetic signature of the *maspin* gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, et al., "Maternal plasma DNA analysis with massively parallel sequencing by ligation for noninvasive prenatal diagnosis of trisomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011), entire document.
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).

(56) References Cited

OTHER PUBLICATIONS

Choo, et al., "A Chromosome 14-specific Human Satellite III DNA Subfamily That Shows Variable Presence on Different Chromosomes 14", Am J. Hum. Genet., 50:706-16 (1992).
Chromosome 14 map, Nature, 409-947-48 (2001).
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet., 15:441-45 (2007).
Conover, Practical Nonparametric Statistics, pp. 295-01 (John Wiley & Sons, NY)(1971).
Costa, et al., "New strategy for prenatal diagnosis of X-linked disorders", N. Engl J. Med., 346:1502 (2002).
Datta, et al., "Sensitive Detection of Occult Breast Cancer by the Reverse-Transcriptase Polymerase Chain Reaction", J. of Clinical Oncology, 12(3): 475-82 (1994).
Dear, et al., "A High-Resolution Metric HAPPY Map of Human Chromosome 14", Genomics, 48:232-41 (1998).
Dennin, "DNA of Free and Complexed Origin in Human Plasma: Concentration and Length Distribution", Klin. Wochenschr., 57:451-56 (1979).
Dhallan et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030, entire document.
Stroun, et al., "Neoplastic Characteristics of the DNA Found in the Plasma of Cancer Patients", Oncology, 46: 318-322 (1989).
Stroun, et al., "Isolation and Characterization of DNA from the Plasma of Cancer Patients", Eur. J. Cancer Clin. Oncol., 23(6)707-12 (1987).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Sullivan, et al., "Evidence for Structural Heterogeneity from Molecular Cytogenetic Analysis of Dicentric Robertsonian Translocations", Am. J. Hum. Genet., 59:167-75 (1996).
Tagle, et al., "An optimized Alu-PCR primer pair for human-specific amplification of YACs and somatic cells hybrids", Human Molecular Genetics, 1(2):121-22 (1992).
Tomilin, et al., "Mechanisms of Chromosome Destabilization in Human Cells", Sov. Sci. Rev. D. Physiochem. Biol., 10:39-89 (1992).
Tong, et al., "Noninvasive prenatal detection of fetal trisomy 18 by epigenetic allelic ratio analysis in maternal plasma: theoretical and empirical considerations", Clin Chern, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684-91 (2011).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Vogelstein, et al., "Digital PGR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Walker, et al., "Human DNA quantitation using Alu element-based polymerase chain reaction", Analytical Biochem., 315:122-28 (2003).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Witt, et al., "An improved, non-isotopic method of screening cells from patients with abnormalities of sexual differentiation for Y chromosomal DNA content", J. Med. Genet., 30:304-07 (1993).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Enders, et al., "Fetal morbidity and mortality after acute human parvovirus B19 infection in pregnancy: prospective evaluation of 1018 cases", Prenatal Diagnosis, 24:513-18 (2004).
Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Xie and Tammi, "CNV-seq, a new method to detect copy number variation using high throughput sequencing", BMC Bioinformatics, 10:80 (2008), doi 10.1186/1471-2105-10-80, p. 1-9.
Search Report dated Oct. 15, 2012 for (PCT/US2011/046981), entire document.
Search Report dated Jan. 20, 2012 for (PCT/US2012/21955), entire document.
Search Report dated May 2, 2012 for PCT/US2011/046935), entire document.
Search Report dated May 10, 2012 for (PCT/US2012/026754), entire document.
Search Report dated May 11, 2012 for (PCT/US2012/022261) entire document.
Search Report dated Feb. 21, 2013 for (PCT/US2011/046963), entire document.
Search Report dated Apr. 19, 2013 for (PCT/US2012/70177), entire document.
Office Action dated Apr. 15, 2013 for U.S. Appl. No. 13/356,133 (inventor A. Oliphant, filed Jan. 23, 2012), entire document.
Office Action dated May 17, 2013 for U.S. Appl. No. 13/356,575 (inventor A. Oliphant, filed Jan. 23, 2012), entire document.
Office Action dated Apr. 5, 2013 for U.S. Appl. No. 13/689,206 (inventor A. Oliphant, filed Nov. 2, 39012), entire document.
Final Office Action dated Jul. 8, 2013 for U.S. Appl. No. 13/689,206 (inventor A. Oliphant, filed Nov. 2, 39012), entire document.
Office Action dated Jul. 5, 2012 for U.S. Appl. No. 13/013,732 (inventor A. Oliphant, filed Jun. 25, 2011), entire document.
Office Action dated Dec. 7, 2012 for U.S. Appl. No. 13/013,732 (inventor A. Oliphant, filed Jun. 25, 2011), entire document.

(56) References Cited

OTHER PUBLICATIONS

Office Action dated Apr. 11, 2013 for U.S. Appl. No. 13/013,732 (inventor A. Oliphant, filed Jun. 25, 2011), entire document.
Office Action dated May 13, 2013 for U.S. Appl. No. 13/407,978 (inventor K. Song, filed Feb. 29, 2012), entire document.
Office Action dated Jul. 8, 2013 for U.S. Appl. No. 13/205,490 (inventor A. Sparks, filed Aug. 8, 2011), entire document.
Office Action dated Mar. 28, 2013 for U.S. Appl. No. 13/687,169 (inventor A. Sparks, filed Nov. 28, 2012), entire document.
Office Action dated Feb. 28, 2013 for U.S. Appl. No. 13/205,570 (inventor A. Sparks, filed Aug. 8, 2011), entire document.
Office Action dated Mar. 14, 2013 for U.S. Appl. No. 13/687,025 (inventor A. Sparks, filed Nov. 28, 2012), entire document.
Office Action dated May 10, 2012 for U.S. Appl. No. 13/293,419 (inventor A. Sparks, filed Nov. 10, 2011), entire document.
Office Action dated Aug. 22, 2012 for U.S. Appl. No. 13/293,419 (inventor A. Sparks, filed Nov. 10, 2011), entire document.
Final Office Action Received on Oct. 12, 2012 for U.S. Appl. No. 13/293,419 (inventor A. Sparks, filed Nov. 10, 2011), entire document.
Advisory Action dated Jan. 29, 2013 for U.S. Appl. No. 13/293,419 (inventor A. Sparks, filed Nov. 10, 2011), entire document.
Office Action dated Feb. 28, 2013 for U.S. Appl. No. 13/245,133 (inventor A. Oliphant, filed Sep. 26, 2011), entire document.
Office Action dated Jun. 13, 2013 for U.S. Appl. No. 13/316,154 (inventor A. Oliphant, filed Dec. 9, 2011), entire document.
Office Action dated Jun. 13, 2013 for U.S. Appl. No. 13/338,963 (inventor A. Oliphant, filed Dec. 28, 2011), entire document.
Office Action dated Feb. 15, 2013 for U.S. Appl. No. 13/689,417 (inventor A. Oliphant, filed Nov. 29, 2012), entire document.
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Margulies, et al., "Genome sequencing in microfabricated high-density picolitre reactors", Nature, 437(15):376-80 and errata (2005).
Mikhaylov, et al., "Changes in the quantity and synthesis of DNA in the nuclei of large decidual cells of rats in the course of their differentiation", Tsitologiia (Cytology),41(6):677-83 (1992).
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Moreno and Gomella, "Circulating Prostate Cancer Cells Detected by Reverse Transcription-Polymerase Chain Reaction (RT-PCR: What do they mean?", Cancer Control Journal, 5(6):1-5 (1998).
Mulcahy, et al., "Plasma DNA K-rase Mutations in Patients with Gastrointestinal Malignancies," Annals New York Academy of Sciences, 25-28 (2006).
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz et al., "Microsatellite alterations in serum DNA of head and neck cancer patients", Nature Medicine, 2(9):1035-37 (1996).
Nelson, et al., "Alu polymerase chain reaction: A method for rapid isolation of human-specific sequence from complex DNA sources," PNAS USA, 86:6686-90 (1989).
Ng, et al., "mRNA of placental origin is readily detectable in maternal plasma", PNAS USA, 100:4748-53 (2003).
Oei, et al., "Clusters of regulatory signals for RNA polymerase II transcription associated with Alu family repeats and CpG islands in human promoters", Genomics, 83:873-82 (2004).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Paolella, et al., "The Alu family repeat promoter has a tRNA-like bipartite structure", EMBO J., 2(5):691-96 (1983).
Papageorgiou, et al., "DNA methylation ratio permits noninvasive prenatal diagnosis of trisomy 21", Nat. Med., 17:510-13(2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Robbins, et al., *Pathologic Basis of Disease 5th Ed.*, Chapter 23, pp. 1071-1088 (1994).
Ronaghi, et al., "A Sequencing Method Based on Real Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Shendure, et al., "Accurate Multiplex Polony Sequencing of an Evolved Bacterial Genome", Science, 309:1728-32 (2005).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Schuster, et al., "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Disease", Cancer, 51:2116-20 (1983).
Simpson and Elias, "Isolating Fetal Cells from Maternal Blood", JAMA, 270(19):2357-61 (1993).
Simpson, et al., "Isolating Fetal Cells in Maternal Circulation for Prenatal Diagnosis", Prenatal Diagnosis, 14:1229-42 (1994).
Simpson, "Is Cell-Free Fetal DNA from Maternal Blood Finally Ready for Prime Time?", Obst & Gynecol., 119(5):1-3 (2012).

(56) References Cited

OTHER PUBLICATIONS

Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Smith, et al.,"Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Ehrich, et al., "Noninvasive detection of fetal trisomy 21 by sequencing of fetal DNA in maternal blood: a study in a clinical setting", Am J. Obstet Gynecol, 2011:204:205 e1-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010), entire document.
Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fournie et al., "Plasma DNA as Cell Death Marker in Elderly Patients", Gerontology, 39:215-221 (1993).
Fowke, Genetic analysis of human DNA recovered from minute amounts of serum and plasma, J. of Immunol. Meth., 180:45-51 (1995).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostatic Carcinoma Clinical Implications", J. of Clin. Oncology, 13(5):1995-200 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Guatelli, et al., "Isothermal, in vitro amplification of nucleic acids by a multienzyme reaction modeled after retroviral replication", PNAS USA, 87(5):1874-78 (1990).
Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Harrell, Regression modeling strategies, §§9.2.2 and 1.10.5 (Springer Vertag)(2001).
Heid, et al., "Real Time Quantitative PCR", Genome Res., 6:986-94 (1996).
Heilig, et al., "The DNA sequence and analysis of human chromosome 14", Nature, 421:601-09 (2003).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
Hosny, et al., "TP53 mutations in circulating fee DNA from Egyptian patients with non-Hodgkin's lymphoma", Cancer Lett., 275(2):234-39 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003), entire document.
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", AM J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010), entire document.
Lo, "Fetal nucleic acids in maternal blood: the promises", Clin. Chem. Lab Med., 50(5):xxx-xxx (DOI 10.1515/CCLM.2011.765) (2011).

(56) References Cited

OTHER PUBLICATIONS

Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Bianchi, et al., "Large Amounts of Cell-free DNAS Are Present in Amniotic Fluid", Clin. Chem., 47(10) 1867-69 (2001).
Centre for Genomics Education, "Changes to Chromosome Structure—Translocations", The Australasian Genetics Resource Book, www.genetics.com, pp. 1-5 (2007).
Chiu, et al., "Non-invasive prenatal diagnosis by single molecule counting technologies", Trends in Genomics, 25(7):324-31 (2009).
Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
Mardis, et al., "The impact of next-qeneration sequencing technology on qenetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action dated Oct. 31, 2013 for U.S. Appl. No. 13/356,575, filed Jan. 23, 2012, inventor Oliphant, entire document.
Office Action dated Jun. 25, 2014 for U.S. Appl. No. 13/689,206, filed Nov. 29, 2012, inventor Oliphant, entire document.
Office Action dated Feb. 11, 2014 for U.S. Appl. No. 13/689,206, filed Nov. 29, 2012, inventor Oliphant, entire document.
Office Action dated Jun. 26, 2014 for U.S. Appl. No. 13/356,133, filed Jan. 23, 2012, inventor Oliphant, entire document.
Office Action dated Oct. 18, 2013 for U.S. Appl. No. 13/356,133, filed Jan. 23, 2012, inventor Oliphant, entire document.
Office Action dated Jul. 31, 2013 for U.S. Appl. No. 13/013,732, filed Jun. 25, 2011, inventor Oliphant, entire document.
Office Action dated Apr. 14, 2014 for U.S. Appl. No. 13/013,732, filed Jun. 25, 2011, inventor Oliphant, entire document.
Office Action dated Feb. 11, 2014 for U.S. Appl. No. 13/405,839, filed Feb. 27, 2012, inventor Oliphant, entire document.
Office Action dated Oct. 25, 2013 for U.S. Appl. No. 13/407,978, filed Feb. 29, 2012, inventor Song, entire document.
Office Action dated Jul. 30, 2014 for U.S. Appl. No. 13/407,978, filed Feb. 29, 2012, inventor Song, entire document.
Office Action dated Jan. 31, 2014 for U.S. Appl. No. 13/605,505, filed Sep. 6, 2012, inventor Struble, entire document.
Office Action dated Aug. 8, 2013 for U.S. Appl. No. 13/605,505, filed Sep. 6, 2012, inventor Struble, entire document.
Office Action dated Aug. 30, 2013 for U.S. Appl. No. 13/687,169, filed Nov. 28, 2012, inventor Sparks, entire document.
Office Action dated May 8, 2014 for U.S. Appl. No. 13/687,169, filed Nov. 28, 2012, inventor Sparks, entire document.
Office Action dated Dec. 10, 2013 for U.S. Appl. No. 13/205,490, filed Aug. 8, 2011, inventor Sparks, entire document.
Office Action dated Jul. 8, 2013 for U.S. Appl. No. 13/205,490, filed Aug. 8, 2011, inventor Sparks, entire document.
Office Action dated Oct. 2, 2013 for U.S. Appl. No. 13/687,025, filed Nov. 28, 2012, inventor Sparks, entire document.
Office Action dated Jul. 16, 2014 for U.S. Appl. No. 13/687,025, filed Nov. 28, 2011, inventor Sparks, entire document.
Office Action dated Aug. 30, 2013 for U.S. Appl. No. 13/205,570, filed Aug. 8, 2011, inventor Sparks, entire document.
Office Action dated May 8, 2014 for U.S. Appl. No. 13/205,570, filed Aug. 8, 2011, inventor Sparks, entire document.
Office Action dated Jul. 14, 2014 for U.S. Appl. No. 13/293,419, filed Nov. 10, 2011, Sparks, entire document.
Office Action dated Jun. 26, 2014 for U.S. Appl. No. 13/205,603, filed Aug. 8, 2011, inventor Sparks, entire document.
Office Action dated Dec. 30, 2013 for U.S. Appl. No. 13/205,603, filed Aug. 8, 2011, inventor Sparks, entire document.
Office Action dated Dec. 11, 2013 for U.S. Appl. No. 13/274,309, filed Oct. 15, 2011, inventor Struble, entire document.
Office Action dated Aug. 30, 2013 for U.S. Appl. No. 13/245,133, filed Sep. 26, 2011, inventor Oliphant, entire document.
Office Action dated Feb. 28, 2013 for U.S. Appl. No. 13/245,133, filed Sep. 26, 2011, inventor Oliphant, entire document.
Office Action dated May 8, 2014 for U.S. Appl. No. 13/245,133, filed Sep. 26, 2011, inventor Oliphant, entire document.
Office Action dated May 12, 2014 for U.S. Appl. No. 13/689,417, filed Nov. 29, 2012, inventor Oliphant, entire document.
Office Action dated Oct. 31, 2013, filed Dec. 9, 2011, inventor Oliphant for U.S. Appl. No. 13/316,154, entire document.
Australian Patent Examination Report No. 1 dated Feb. 20, 2014 for 2011285512, entire document.
Australian Patent Examination Report No. 1 dated Mar. 4, 2014 for 2011285518, entire document.
Australian Patent Examination Report No. 1 dated Feb. 7, 2014 for 2011285477, entire document.
EPO Examination Report dated Nov. 21, 2013 for App. No. 11745880.2, entire document.
EPO Examination Report dated Nov. 21, 2013 for App. No. 11745881.1, entire document.
EPO Examination Report dated Nov. 28, 2013 for App. No. 11745883.6, entire document.
Search Report dated Sep. 12, 2013 for PCT/US 2012/026754, entire document.
Search Report dated Nov. 15, 2013 for PCT/US 2013/51310, entire document.
Search Report dated May 14, 2013 for PCT/US 2014/17092, entire document.
Nicolaides, K.H. et al. (2014, e-published Dec. 11, 2013). "Assessment of fetal sex chromosome aneuploidy using directed cell-free DNA analysis," *Fetal Diagn Ther* 35(1):1-6.

\* cited by examiner

STATISTICAL ANALYSIS FOR NON-INVASIVE SEX CHROMOSOME ANEUPLOIDY DETERMINATION

PRIORITY

This application is a continuation-in-part of U.S. Ser. No. 13/790,642 filed Mar. 8, 2013 and is a continuation-in-part of U.S. Ser. No. 13/338,963, filed Dec. 28, 2011, which is a continuation-in-part of U.S. Ser. No. 13/316,154, filed Dec. 9, 2011, which claims priority to U.S. Ser. No. 61/436,135, filed Jan. 25, 2011, each of which is incorporated by reference herein in its entirety.

FIELD OF THE INVENTION

This invention relates to statistical analysis for non-invasive sex determination of a fetus or of X and Y chromosomal frequency abnormalities by detecting and determining the relative contribution of genetic sequences from the X and Y chromosomes in view of the percent fetal contribution in a maternal mixed sample.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including syndromes caused by chromosomal aneuploidy (e.g., Down syndrome) and those caused by germline mutations resulting in either monogenic or polygenic diseases or disorders. Detection of both gross chromosomal abnormalities, such as trisomies, translocations and large insertions or deletions, and single gene traits, such as single gene mutations or polymorphisms associated with Rh blood group status, autosomal dominant or X-linked disorders, or autosomal recessive disorders are useful in detecting actual and potential pathologies and disorders that may affect a fetus. For example, chromosomal abnormalities such as trisomies 13, 18, and 21, Robertsonian translocations, and larger deletions such as those found on chromosome 22 in DiGeorge syndrome all impact significantly on fetal health.

Although conventional technology provides detection methods for these different genetic abnormalities, until recently different genetic abnormalities required different techniques to interrogate different classes of mutations. For example, conventional methods of prenatal diagnostic testing for chromosomal aneuploidy required removal of a sample of fetal cells directly from the uterus for genetic analysis, using either chorionic villus sampling (CVS) between 11 and 14 weeks gestation or amniocentesis after 15 weeks. However, such invasive procedures carry a risk of miscarriage of around one percent (see Mujezinovic and Alfirevic, Obstet. Gynecol., 110:687-694 (2007)). Other analyses of fetal cells typically involve karyotyping or fluorescent in situ hybridization (FISH) and do not provide information about single gene traits; thus, additional tests are required for identification of single gene diseases and disorders.

Non-invasive detection of paternally-inherited DNA sequences that are absent in the maternal genome, e.g., Y chromosomal sequences for fetal sexing and the RHD gene for blood group genotyping, has been possible since the mid-1990s. However, the recent emergence of single molecule counting technologies—such as digital polymerase chain reaction and particularly massively parallel sequencing—has allowed circulating fetal DNA to be used for the non-invasive prenatal diagnosis of fetal chromosomal aneuploidies and monogenic diseases, yet other fetal anomalies and/or quality control parameters for testing remain unaddressed.

There is a need in the art for accurate determination of fetal sex, X chromosomal frequency and Y chromosomal frequency. The present invention addresses this need.

SUMMARY OF THE INVENTION

This Summary is provided to introduce a selection of concepts in simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

In one aspect, the methods utilize multiplexed amplification and detection of selected nucleic acid regions on the sex chromosomes and one or more autosomes (i.e., autosomes) to calculate the frequency of the X and Y chromosomes in relation to the percent fetal nucleic acid contribution in a maternal mixed sample. Relative quantities of the selected nucleic acid regions are determined for genomic regions of interest (e.g., sex chromosomal sequences as well as sequences from one or more autosomal chromosome sequences) using the analytical methods as described herein. Such methods are used to determine the sex of a fetus, possible X and Y chromosomal aneuploidies and intersex mosaicisms, as well as to assess the likelihood of contamination of the maternal mixed sample.

[TBD when the claims are finalized]

These and other aspects, features and advantages will be provided in more detail as described herein.

DETAILED DESCRIPTION OF THE INVENTION

Figure 1:
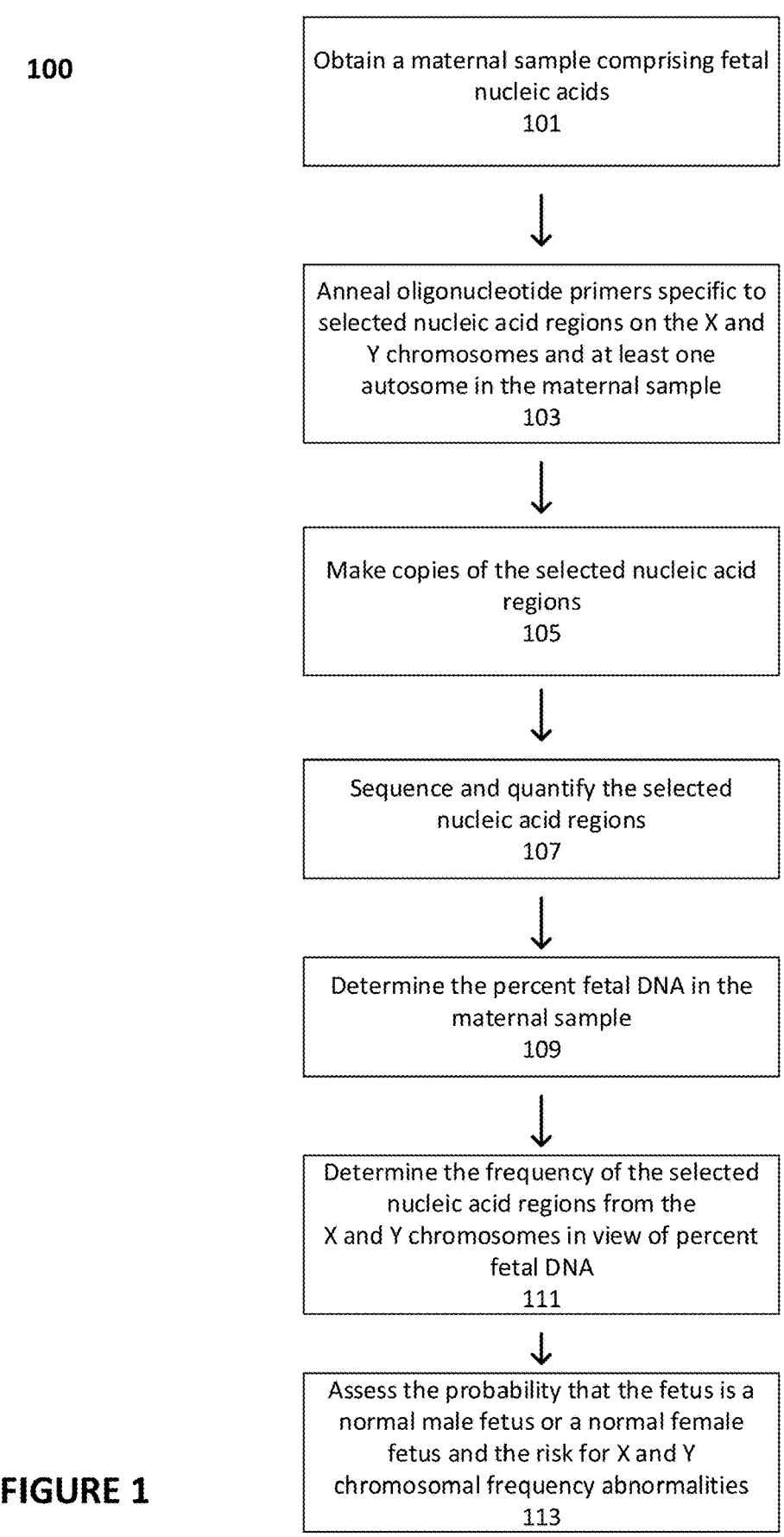
FIG. 1 is a simplified flow chart of one assay method according to the present invention.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "*Oligonucleotide Synthesis: A Practical Approach*" IRL Press, London (1984); Nelson and Cox, Lehninger, *Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

It should be noted that as used herein and in the appended claims, the singular forms "a," "an," and "the" include plural referents unless the context clearly dictates otherwise. Thus, for example, reference to "a nucleic acid region" refers to one, more than one, or mixtures of such regions, and reference to "a method" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those limits are also included in the invention.

All publications mentioned herein are incorporated by reference for all purposes including the purpose of describing and disclosing formulations and methodologies that might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication method performed in vitro as compared to its starting amount.

The term "chromosomal abnormality" refers to any genetic variant for all or part of a chromosome. The genetic variants may include but not be limited to any copy number variant such as duplications or deletions, translocations, inversions, and mutations. The term also includes chromosomal mosaicism in fetal or maternal tissue.

The term "diagnostic tool" as used herein refers to any composition or method of the invention used in, for example, a system in order to carry out a diagnostic test or assay on a patient sample.

The term "intersex mosaicism" or "sex chromosome mosaicism" or "sex chromosome mosaic" refers to the presence of two or more populations of cells with different sex chromosome genotypes in one individual. Intersex mosaicisms arise when some cells in an individual have, e.g., two X chromosomes (XX) and other cells in the individual have one X chromosome and one Y chromosome (XY); when some cells in an individual have one X chromosome (XO) and other cells in the individual have one X chromosome and one Y chromosome (XY); or when some cells in an individual have two X chromosomes and one Y chromosome (XXY) and other cells in the individual have one X chromosome and one Y chromosome (XY).

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "likelihood" refers to any value achieved by directly calculating likelihood or any value that can be correlated to or otherwise indicate a likelihood.

The terms "locus" and "loci" as used herein refer to a nucleic acid region of known location in a genome.

The term "maternal sample" as used herein refers to any sample taken from a pregnant female that comprises both fetal and maternal nucleic acids (e.g., DNA). Preferably, maternal samples for use in the invention are obtained through relatively non-invasive means, e.g., phlebotomy or other standard techniques for extracting peripheral samples from a subject.

"Microarray" or "array" refers to a solid phase support having a surface, preferably but not exclusively a planar or substantially planar surface, that carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., isolation of specific nucleic acids or sequence analysis of one or more biological molecules using a microarray.

By "non-polymorphic" or "polymorphism-agnostic", when used with respect to detection of selected nucleic acid regions, is meant detection of a nucleic acid region, which may contain one or more polymorphisms, but in which the detection is not reliant on detection of the specific polymorphism within the region. Thus a selected nucleic acid region may contain a polymorphism, but detection of the region using the methods of the invention is based on occurrence of the region rather than the presence or absence of a particular polymorphism in that region.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes in a locus that may be indicative of that particular loci, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleotide for detection of a specific nucleic acid region.

The term "research tool" as used herein refers to any method of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selected nucleic acid region" as used herein refers to a nucleic acid region corresponding to an individual chromosome. Selected nucleic acid regions may be directly isolated and enriched from the sample for detection, e.g., based on hybridization and/or other sequence-based techniques, or they may be amplified using the sample as a template prior to detection of the sequence.

The terms "selective amplification" and "selectively amplify" and the like refer to an amplification procedure that depends in whole or in part on hybridization of an oligo to a sequence in a selected nucleic acid region. In certain selective amplifications, the primers used for amplification are complementary to a selected nucleic acid region. In other selective amplifications, the primers used for amplification are universal primers, but they only result in a product if a region of the nucleic acid used for amplification is complementary to a selected nucleic acid region of interest.

The terms "sequencing" and "sequence determination" and the like as used herein refer generally to any and all biochemical methods that may be used to determine the order of nucleotide bases in a nucleic acid.

The terms "specifically binds" and "specific binding" and the like as used herein, when referring to a binding partner (e.g., a nucleic acid probe or primer, antibody, etc.) result in the generation of a statistically significant positive signal under the designated assay conditions. Typically the interaction will subsequently result in a detectable signal that is at least twice the standard deviation of any signal generated as a result of undesired interactions (background).

The term "universal", when used to describe an amplification procedure, refers to the use of a single primer or set of primers for a plurality of amplification reactions. For example, in the detection of 96 different target sequences, all the templates may share identical universal priming sequences, allowing for the multiplex amplification of the 96 different sequences using a single set of primers. The use of such primers greatly simplifies multiplexing in that only two primers are needed to amplify a plurality of selected nucleic acid sequences. The term "universal" when used to describe a priming site is a site to which a universal primer will hybridize. It should also be noted that "sets" of universal priming sequences/primers may be used. For example, in highly multiplexed reactions, it may be useful to use several sets of universal sequences, rather than a single set; for example, 96 different nucleic acids may have a first set of universal priming sequences, and the second 96 a different set of universal priming sequences, etc.

The Invention in General

The present invention provides improved methods for identifying copy number variants of the X and Y chromosomes. The methods of the invention are useful for determining the sex of a fetus, assessing the probability of an X chromosome aneuploidy, a Y chromosome aneuploidy or sex chromosome mosaicism in a fetus, or for determining possible contamination of a maternal sample. In some aspects, the methods of the invention are also useful for detecting X chromosome aneuploidies or mosaicisms in the mother.

The assay methods of the invention include selective enrichment of selected nucleic acid regions from the X chromosome and the Y chromosome and one or more non-sex reference chromosomes (autosomes). A distinct advantage of the invention is that the selected nucleic acid regions can be further analyzed using a variety of detection and quantification techniques, including but not limited to hybridization techniques, digital PCR, and, preferably, high-throughput sequencing determination techniques. Primers can be designed against any number of selected nucleic acid regions for any chromosome in addition to the X and Y chromosomes. Although amplification prior to the identification and quantification of the selected nucleic acid regions is not mandatory, limited amplification prior to detection is preferred.

The present invention is an improvement over more random techniques such as massively parallel shotgun sequencing (e.g., random sequencing) or the use of random digital PCR that have been used recently to detect copy number variations in maternal samples such as maternal blood. The aforementioned approach relies upon sequencing of all or a statistically significant population of DNA fragments in a sample, followed by mapping of or otherwise associating or aligning the fragments to their appropriate chromosomes. The identified fragments are then compared against each other or against some other reference (e.g., a sample with a known euploid chromosomal complement) to determine copy number variation of particular chromosomes. Random or shotgun sequencing methods are inherently inefficient as compared to the present invention, as the data generated on the chromosomal regions of interest constitute only a minority of the data that is generated.

Techniques that are dependent upon a very broad sampling of DNA in a sample provide a broad coverage of the DNA analyzed, but in fact are sampling the DNA contained within a sample on a 1× or less basis (i.e., subsampling). In contrast, the selective amplification and/or enrichment techniques (such as hybridization) used in the present methods provide depth of coverage of only the selected nucleic acid regions; and as such provide a "super-sampling" of the selected nucleic acid regions with an average sequence coverage of preferably 2× or more, more preferably sequence coverage of 100× of more, 200× or more, 250× or more, 500× or more, 750× or more or even more preferably sequence coverage of 1000× or more of the selected nucleic acid regions.

Thus, in the assays of the present invention, the substantial majority of sequences analyzed for quantification are informative of the presence of one or more selected nucleic acid regions on the X and Y chromosome and one or more autosomes. The methods of the invention do not require analysis of large numbers of sequences that are not from the chromosomes of interest and that do not provide information on the relative quantity of the chromosomes of interest.

Detecting and Quantifying the Sex Chromosomes

The present invention provides methods for determining frequency of X and Y sequences in a maternal sample. These frequencies can be used, e.g., to determine fetal sex, and/or for identifying X chromosomal aneuploidies, Y chromosomal aneuploidies and/or sex chromosome mosaicisms. The samples are maternal samples comprising both maternal and fetal DNA such as maternal blood samples (i.e., whole blood, serum or plasma). The methods enrich and/or isolate and amplify one or, preferably, several to many selected nucleic acid regions in a maternal sample that correspond to the X and Y chromosomes and one or more autosomes that are used to determine the presence or absence and/or relative quantity or frequency of X and Y chromosomal sequences in view of the percent of fetal DNA present in the sample. As described in detail supra, the methods of the invention preferably employ one or more selective amplification, ligation or enrichment (e.g., using one or more nucleic acids that specifically hybridize to the selected nucleic acid regions) steps to enhance the content of the selected nucleic acid regions in the sample. The selective amplification, ligation and/or enrichment steps typically include mechanisms to engineer copies of the selected nucleic acid regions for further isolation, amplification and analysis. This selective approach is in direct contrast to the random amplification approach used by other techniques, e.g., massively parallel shotgun sequencing, as such techniques generally involve random amplification of all or a substantial portion of the genome.

In certain aspects, the methods of the invention can identify maternal aneuploidies, including maternal mosaicism. The frequencies of the maternal X and Y chromosomal material must be analyzed in view of the fetal DNA in the maternal sample. The determined risk profiles of such maternal aneuploidies may vary depending on the particular aneuploidy. For example, in the case where a mother is an XX/XO mosaic, the determined probability will be dependent upon the level of maternal mosaicism, the tissues affected, as well as the percent fetal in the maternal sample.

The examples above demonstrate that if one is to detect specific nucleic acids present at such a low percentage robustly through the methods described herein, the variation in the measurement of the extra chromosome has to be significantly less than the percent increase of the extra chromosome.

FIG. 1 is a simplified flow chart of one method 100 according to the present invention. In a first step, a maternal sample is obtained 101. The maternal sample comprises both maternal and fetal nucleic acids. Maternal samples may be any sample taken from a pregnant female that comprises both fetal and maternal nucleic acids (e.g., DNA). Preferably, maternal samples for use in the invention are cell free, and obtained through relatively non-invasive means, such as phlebotomy or other standard techniques for extracting peripheral samples from a subject.

In a next step 103, oligonucleotide primers specific to selected nucleic acid regions on the X chromosome and on the Y chromosome and on at least one autosome (and preferably more than one autosome) are annealed to the selected nucleic acids in the maternal sample. The oligonucleotide primers are used to selectively amplify the selected nucleic acid regions in step 105 to produce copies of the selected nucleic acid regions. As described in detail infra, the selected nucleic acid regions are subjected to a selective amplification step, but may also be subjected to a universal amplification step either before the selective amplification step, or, preferably, after the selective amplification step. In addition, one or more enrichment steps may be performed as described infra. Also, as an alternative to amplification, an enrichment step may be performed such as by selective hybridization, which separates the selected nucleic acid regions from the other nucleic acids in the sample.

In step 107, the amplified or copied selected nucleic acid regions are then sequenced and quantified. Preferred embodiments utilize high throughput or next generation sequencing techniques, though other techniques optionally may be used, as described infra. High throughput sequencing allows for massive parallelization of the sequence determination and quantification step.

In step 109, the percent of fetal DNA in the maternal sample is determined. Next, in step 111, the frequencies of the selected nucleic acid regions from the X chromosome and the Y chromosome are determined in view of the percent fetal DNA determined in step 109. As described in detail herein, the frequency of the selected nucleic acid regions from the X chromosome and the Y chromosome in view of percent fetal permits at step 113 the assessment of the risk for X chromosomal frequency abnormalities, such as those arising from X chromosomal aneuploidy, X chromosomal mosaicism or X chromosomal contamination and/or Y chromosomal frequency abnormalities, such as those arising from Y chromosomal aneuploidy, Y chromosomal mosaicism or Y chromosomal contamination of a maternal sample from a woman carrying a female fetus.

Thus, in general, selected nucleic acid regions corresponding to multiple loci on the X chromosome are detected and summed to determine the relative frequency of X chromosomes in the maternal sample. Selected nucleic acid regions corresponding to multiple loci on one or more autosomes are detected and summed to determine the relative frequency of the one or more additional chromosomes in the maternal sample which permits calculation of percent fetal. Once percent fetal is determined, the frequency of the X chromosome is viewed in light of the percent fetal in order to assess whether an X chromosomal abnormality exists. Similarly, selected nucleic acid regions corresponding to multiple loci on the Y chromosome are detected and summed to determine the relative frequency of the Y chromosome in the maternal sample and the frequency of the Y chromosome is viewed in light of the percent fetal in order to assess whether a Y chromosomal abnormality exists.

The methods of the invention analyze multiple selected nucleic acid regions representing selected loci on at least three chromosomes: the X chromosome, the Y chromosome and at least one autosome and the relative frequency of each selected nucleic acid region is analyzed and independently quantified to determine a relative frequency for each selected nucleic acid region in the sample. The sums of the selected nucleic acid regions in the sample are used to determine percent fetal DNA in the sample and are compared to determine statistically whether a chromosomal aneuploidy or other chromosomal abnormality exists in relation to X and/or the Y chromosomal sequences.

In another aspect, subsets of selected nucleic acid regions on each chromosome are analyzed to determine whether a chromosomal abnormality or chromosomal frequency abnormality exists. The selected nucleic acid region frequencies can be summed for a particular chromosome, and the summations of the selected nucleic acid regions used to determine abnormalities. This aspect of the invention sums the frequencies of the individual selected nucleic acid regions from each chromosome and then compares the sum of the selected nucleic acid regions on the X chromosome to one or more non-sex chromosomes and compares the sum of the selected nucleic acid regions on the Y chromosome to one or more autosomes. The subsets of selected nucleic acid regions can be chosen randomly but with sufficient numbers to yield a statistically significant result in determining whether a chromosomal abnormality exists. Multiple analyses of different subsets of selected nucleic acid regions can be performed on a maternal sample to yield more statistical power. For example, if there are 100 selected nucleic acid regions for chromosome Y and 100 selected nucleic acid regions for chromosome 2, a series of analyses could be performed that evaluate fewer than 100 regions for each of the chromosomes. For example, a series of analyses could be performed that evaluate less than 50 regions, such as less than 30 regions, less than or equal to 16 regions, less than 10 regions or 8 regions. In another aspect, particular selected nucleic acid regions can be selected on each chromosome that are known to have less variation between samples, or the data used for determination of chromosomal frequency may be limited, e.g., by ignoring the data from selected nucleic acid regions with very high or very low frequencies within a sample.

In yet another aspect, the ratio of the frequencies of the selected nucleic acid regions are compared to a reference mean ratio that has been determined for a statistically significant population of genetically euploid subjects, i.e., subjects that do not have an X chromosomal abnormality or a Y chromosomal abnormality.

It should be understood by those with skill in the art that the methods for determining the frequency of the X and the Y chromosome in view of the percent fetal DNA in a maternal sample may be combined with other non-invasive prenatal diagnostic techniques, such as those techniques that assess the risk of a fetal aneuploidy of autosomes, or techniques that detect polymorphic sequences in the fetus.

Assay Methods

A number of different assay methods may be employed in the present invention, including assays using sets of oligonucleotides consisting of fixed oligonucleotides only, or sets of oligonucleotides consisting of fixed oligonucleotides and one or more bridging oligonucleotides. Additionally, the oligonucleotides in a set may hybridize to the selected nucleic acid sequences immediately adjacent to one another where they may be ligated, or oligonucleotides in a set may not hybridize to the selected nucleic acid sequences immediately adjacent to one another, and thus a primer extension reaction using a polymerase and dNTPs is employed before ligation of the oligonucleotides in a set. FIG. 2 through 7 illustrate some exemplary assay methods.

Figure 2:
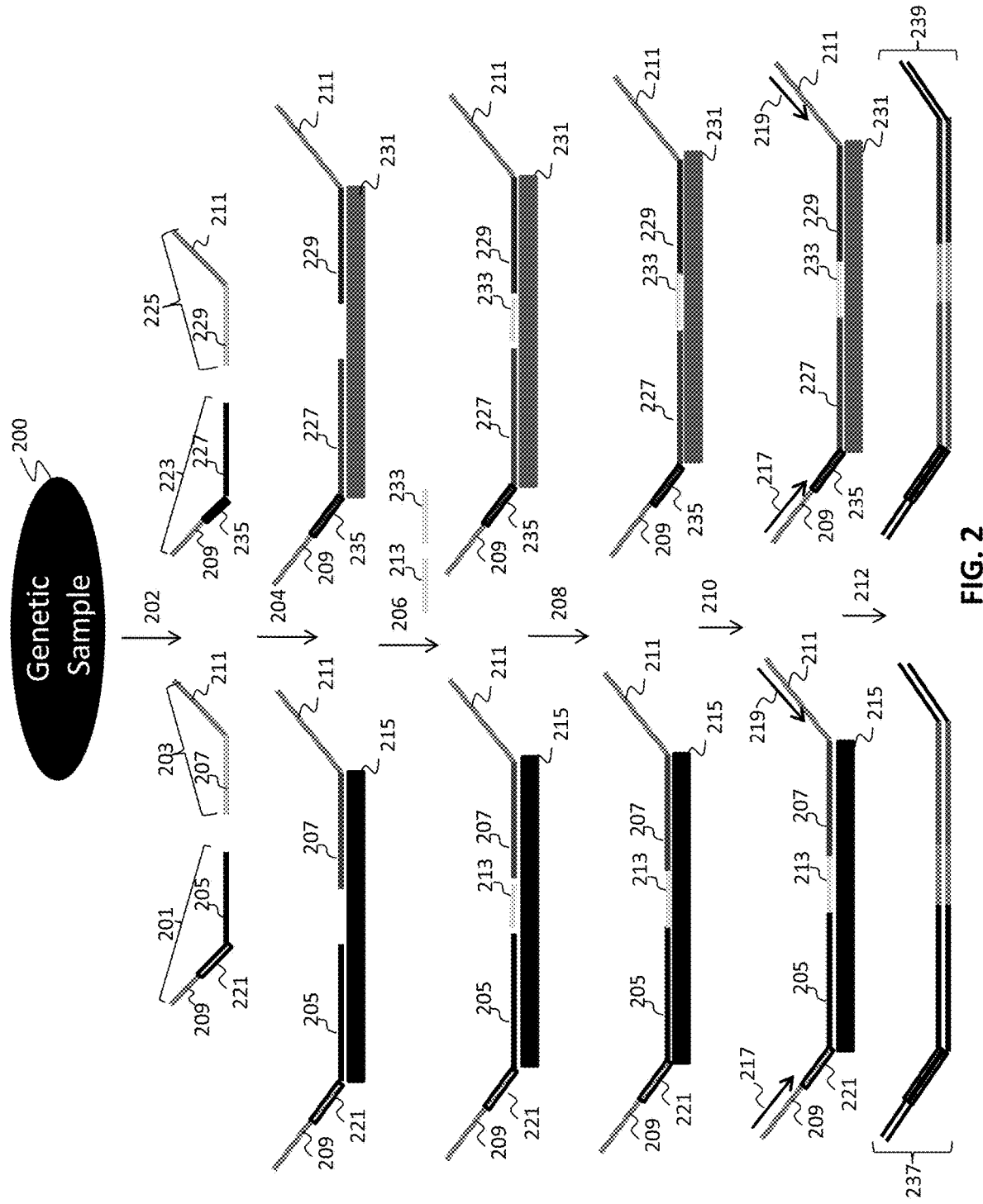
FIG. 2 illustrates a multiplexed assay system for detection of two or more selected nucleic acid regions.

FIG. 2 illustrates one exemplary method embodiment where two different selected nucleic acid regions are detected in a single tandem reaction assay. Such method embodiments, assay systems and related embodiments are described in detail in, e.g., U.S. Ser. No. 13/013,732, filed Jan. 25, 2011; Ser. No. 13/245,133, filed Sep. 26, 2011; Ser. No. 13/205,570, filed Aug. 8, 2011; Ser. No. 13/293,419, filed Nov. 10, 2011; Ser. No. 13/205,409, filed Aug. 8, 2011; Ser. No. 13/205,603, filed Aug. 8, 2011; Ser. No. 13/407,978, filed Feb. 29, 2012; Ser. No. 13/274,309, filed Oct. 15, 2011; Ser. No. 13/316,154, filed Dec. 9, 2011, and Ser. No. 13/338,963, filed Dec. 28, 2011, all of which are incorporated herein in their entirety. Two sets of fixed sequence oligonucleotides (201 and 203, 223 and 225) that specifically hybridize to two different selected nucleic acid regions 215, 231 are introduced 202 to a genetic sample and allowed to hybridize 204 to the respective selected nucleic acid regions. Each set of fixed sequence oligonucleotides comprises an oligonucleotide 201, 223 having a sequence specific region 205, 227, a universal primer region 209 and an index region 221, 235. The other fixed sequence oligonucleotide in a set comprises a sequence specific region 207, 229 and a universal primer region 211. The fixed sequence oligonucleotides generally range in size from about 30-200 nucleotides in length, or from about 30-150 nucleotides in length, or from about 35-120 nucleotides in length, or from about 40-70 nucleotides in length. If bridging oligonucleotides are employed, the bridging oligonucleotides generally range in size from about 4 to about 80 nucleotides in length, or from about 4 to about 60 nucleotides in length, or from about 5 to about 50 nucleotides in length, or from about 7 to about 40 nucleotides in length, or from about 10 to about 40 nucleotides in length, or from about 12 to about 30 nucleotides in length, or from about 15 to about 25 nucleotides in length.

Following hybridization, the unhybridized fixed sequence oligonucleotides are preferably separated from the remainder of the sample (step not shown). Bridging oligos 213, 233 are introduced to the hybridized pair of fixed sequence oligonucleotide/nucleic acid regions and allowed to hybridize 206 to these regions. Although shown in FIG. 2 as two different bridging oligonucleotides, in fact the same bridging oligonucleotide may be suitable for both hybridization events (assuming the sequences are the same or substantially similar), or they may be two oligonucleotides from a pool of degenerating-sequence oligonucleotides. The hybridized oligonucleotides are ligated 208 to create a contiguous nucleic acid spanning and complementary to each selected nucleic acid region of interest. It should be noted that although this particular embodiment exemplifies a method using two fixed sequence oligonucleotides and a bridging oligonucleotide to amplify each selected nucleic acid region, methods that use only two fixed sequence oligonucleotides that hybridize immediately adjacent to one another may be employed, or methods that use only two fixed sequence oligonucleotides that do not hybridize immediately adjacent to one another, but where a "gap" is filled using a polymerase and dNTPs, may be employed.

Following ligation, universal primers 217, 219 are introduced to amplify 210 the ligated oligonucleotides to create 212 amplification products 237, 239 that comprise the sequence of the selected nucleic acid regions of interest. These amplification products 237, 239 are isolated (optionally), detected (i.e., sequenced) and quantified to provide information on the presence and amount of the selected nucleic acid regions in the sample.

Numerous amplification methods may be used to selectively amplify the selected nucleic acid regions that are analyzed in the methods of the invention, increasing the copy number of the selected nucleic acid regions in a manner that allows preservation of the relative quantity of the selected nucleic acid regions in the initial sample. Although not all combinations of amplification and analyses are described herein in detail, it is well within the skill of those in the art to utilize different, comparable amplification and/or analysis methods to analyze the selected nucleic acid regions consistent with this specification, as such variations should be apparent to one skilled in the art upon reading the present disclosure.

Amplification methods useful in the present invention include but are not limited to, polymerase chain reaction (PCR) (U.S. Pat. Nos. 4,683,195 and 4,683,202; and described in *PCR Technology: Principles and Applications for DNA Amplification*, ed. H. A. Erlich, Freeman Press, NY, N.Y., 1992); ligase chain reaction (LCR) (Wu and Wallace, Genomics 4:560, (1989); Landegren et al., Science 241: 1077 (1988)); strand displacement amplification (SDA) (U.S. Pat. Nos. 5,270,184 and 5,422,252); transcription-mediated amplification (TMA) (U.S. Pat. No. 5,399,491); linked linear amplification (LLA) (U.S. Pat. No. 6,027,923); self-sustained sequence replication (Guatelli et al., PNAS USA, 87:1874 (1990) and WO90/06995); selective amplification of target polynucleotide sequences (U.S. Pat. No. 6,410,276); consensus sequence primed polymerase chain reaction (CP-PCR) (U.S. Pat. No. 4,437,975); arbitrarily primed polymerase chain reaction (AP-PCR) (U.S. Pat. Nos. 5,413,909 and 5,861,245); and nucleic acid based sequence amplification (NASBA) (see, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880; isothermal amplification methods such as SDA, described in Walker et al., Nucleic Acids Res. 20(7):1691-6 (1992); and rolling circle amplification, described in U.S. Pat. No. 5,648,245. Yet other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In preferred aspects DNA is amplified by multiplex locus-specific PCR. In some aspects the DNA is amplified using adaptor-ligation and single primer PCR. Other available methods of amplification include balanced PCR (Makrigiorgos et al., Nat. Biotechnol., 20:936-39 (2002)) and self-sustained sequence replication (Guatelli et al., PNAS USA, 87:1874 (1990)). Based on such methodologies, a person skilled in the art can readily design primers in any suitable regions 5' and 3' to a selected nucleic acid region of interest. Such primers may be used to amplify DNA of any length so long that it contains the selected nucleic acid region of interest in its sequence.

The length of the selected nucleic acid regions chosen is long enough to provide enough sequence information to distinguish the selected nucleic acid regions from one another. Generally, a selected nucleic acid region is at least about 16 nucleotides in length, and more typically, a selected nucleic acid region is at least about 20 nucleotides in length. In a preferred aspect of the invention, the selected nucleic acid regions are at least about 30 nucleotides in length. In a more preferred aspect of the invention, the selected nucleic acid regions are at least about 32, 40, 45, 50, or 60 nucleotides in length. In other aspects of the invention, the selected nucleic acid regions can be about 100, 150 or up to 200 in length.

In some aspects, the selective amplification process uses one or a few rounds of amplification with primer pairs comprising nucleic acids complementary to the selected nucleic acid regions (i.e., a sequence-specific amplification process). In other aspects, the selective amplification comprises an initial linear amplification step (also a sequence-specific amplification process). Linear amplification methods can be particularly useful if the starting amount of DNA is limited. Linear amplification increases the amount of DNA molecules in a way that is representative of the original DNA content, which helps to reduce sampling error in cases such as the present invention where accurate quantification of the selected nucleic acid regions is needed.

Thus, in preferred aspects, a limited number of cycles of sequence-specific amplification are performed on the starting maternal sample comprising cell free DNA. The number of cycles is generally less than that used for a typical PCR amplification, e.g., 5-30 cycles or fewer.

The oligonucleotides in the sets of oligonucleotides are designed to hybridize to the sample in a sequence-specific manner and to amplify the selected nucleic acid regions. The primers for selective amplification are preferably designed to 1) efficiently amplify the selected nucleic acid regions from the chromosome(s) of interest; 2) have a predictable range of expression from maternal and/or fetal sources in different maternal samples; and 3) be distinctive to the selected nucleic acid regions, i.e., not amplify non-selected nucleic acid regions. The primers or probes may be modified with an end label at the 5' end (e.g., with biotin) or elsewhere along the primer or probe such that the amplification products can be purified or attached to a solid substrate (e.g., bead or array) for further isolation or analysis. In a preferred aspect, the primers are engineered to have, e.g., compatible melting temperatures to be used in multiplexed reactions that allow for the amplification of many selected nucleic acid regions such that a single reaction yields multiple DNA copies from different selected nucleic acid regions and preferably all selected nucleic acid regions. Amplification products from the selective amplification may then be further amplified with standard PCR methods or with linear amplification.

Cell free DNA can be isolated from, e.g., whole blood, plasma, or serum from a pregnant woman, and incubated with primers engineered to amplify a set number of selected nucleic acid regions that correspond to chromosomes of interest. Preferably, the number of primer pairs used for initial amplification of X chromosome-specific sequences (and thus the number of selected nucleic acid regions on the X chromosome) will be 8 or more, such as 16 or more, 32 or more, 48 or more, or 96 or more. Similarly, the number of primer pairs used for initial amplification of Y chromosome-specific sequences (and thus the number of selected nucleic acid regions on the Y chromosome) and on each of the one or more autosomal reference chromosomes will be 8 or more, such as 16 or more, 32 or more, 48 or more, or 96 or more. Each of the primer pairs corresponds to a single selected nucleic acid region, and the primer pairs are optionally tagged for identification (e.g., by used of indices or indexes as described supra) and/or isolation (e.g., comprise a nucleic acid sequence or chemical moiety that is utilized for capture). A limited number of amplification cycles, preferably 10 or fewer, are performed. The amplification products (the amplified selected nucleic acid regions) are optionally subsequently isolated by methods known in the art. For example, when the primers are linked to a biotin molecule, the amplification products can be isolated via binding to avidin or streptavidin on a solid substrate. The amplification products may then be subjected to further biochemical processes such as additional amplification with other primers (e.g., universal primers) and/or detection techniques such as sequence determination and hybridization.

Efficiencies of amplification may vary between selected nucleic acid regions and between cycles so that in certain systems normalization (as described infra) may be used to ensure that the products from the amplification of the selected nucleic acid regions are representative of the nucleic acid content of the sample. One practicing the methods of the invention can mine the data regarding the relative frequency of the amplified products to determine variation in the selected nucleic acid regions, including variation in selected nucleic acid regions within a sample and/or between selected nucleic acid regions in different samples (particularly from the same selected nucleic acid regions in different samples) to normalize the data.

As an alternative to selective amplification, selected nucleic acid regions may be enriched by hybridization techniques (e.g., capture hybridization or hybridization to an array), optionally followed by one or more rounds of amplification. Optionally, the hybridized or captured selected nucleic acid regions are released (e.g., by denaturation) prior to amplification and sequence determination. The selected nucleic acid regions can be isolated from a maternal sample using various methods that allow for selective enrichment of the selected nucleic acid regions used in analysis. The isolation may be a removal of DNA in the maternal sample not used in analysis and/or removal of any excess oligonucleotides used in the initial enrichment or amplification step. For example, the selected nucleic acid regions can be isolated from the maternal sample using hybridization techniques (enrichment), e.g., captured using binding of the selected nucleic acid regions to complementary oligos on a solid substrate such as a bead or an array, followed by removal of the non-bound nucleic acids from the sample. In another example, when a precircle-type probe technique is used for selective amplification (see, e.g., Barany et al., U.S. Pat. Nos. 6,858,412 and 7,556,924 and FIG. 7), the circularized nucleic acid products can be isolated from the linear nucleic acids, which are subject to selective degradation. Other useful methods of isolation will be apparent to one skilled in the art upon reading the present specification.

The selectively-amplified copies of the selected nucleic acid regions optionally may be amplified in a universal amplification step following the selective amplification (or enrichment step), either prior to or during the detection step (i.e., sequencing or other detection technology). In performing universal amplification, universal primer sequences added to the copied selected nucleic acid region in the selective amplification step are used to further amplify the selected nucleic acid regions in a single universal amplification reaction. As described, universal primer sequences may be added to the copied selected nucleic acid regions during the selective amplification process, if performed, by using primers for the selective amplification step that have universal primer sequences so that the amplified copies of the selected nucleic acid regions incorporate the universal priming sequence. Alternatively, adapters comprising universal amplification sequences may be ligated to the ends of the selected nucleic acid regions following amplification or enrichment, if performed, and isolation of the selected nucleic acid regions from the maternal sample.

Bias and variability can be introduced into a sample during DNA amplification, and this is known to happen during polymerase chain reaction (PCR). In cases where an amplification reaction is multiplexed, there is the potential that selected nucleic acid regions will amplify at different rates or efficiencies, as each set of primers for a given selected nucleic acid region may behave differently based on the base composition of the primer and template DNA, buffer conditions, or other conditions. A universal DNA amplification for a multiplexed assay system generally introduces less bias and variability. Another technique to minimize amplification bias involves varying primer concentrations for different selected nucleic acid regions to limit the number of sequence specific amplification cycles in the selective amplification step. The same or different conditions (e.g., polymerase, buffers, and the like) may be used in the amplification steps, e.g., to ensure that bias and variability is not inadvertently introduced due to experimental conditions.

In a preferred aspect, a small number (e.g., 1-10, preferably 3-5) of cycles of selective amplification or nucleic acid enrichment is performed, followed by universal amplification using universal primers. The number of amplification cycles using universal primers will vary, but will preferably be at least 5 cycles, more preferably at least 10 cycles, even more preferably 20 cycles or more. By moving to universal amplification following one or a few selective amplification cycles, the bias of having certain selected nucleic acid regions amplify at greater rates than others is reduced.

Optionally, the methods include a step between the selective amplification and universal amplification to remove any excess nucleic acids that are not specifically amplified in the selective amplification. The whole product or an aliquot of the product from the selective amplification may be used for the universal amplification.

The universal regions of the primers used in the methods are designed to be compatible with conventional multiplexed methods that analyze large numbers of nucleic acids simultaneously in one reaction in one vessel. Such "universal" priming methods allow for efficient, high volume analysis of the quantity of nucleic acid regions present in a maternal sample, and allow for comprehensive quantification of the presence of nucleic acid regions within such a maternal sample for the determination of aneuploidy.

Examples of universal amplification methods include, but are not limited to, multiplexing methods used to amplify and/or genotype a variety of samples simultaneously, such as those described in Oliphant et al., U.S. Pat. No. 7,582,420, which is incorporated herein by reference.

In certain aspects, the assay system of the invention utilizes one of the following combined selective and universal amplification techniques: (1) the ligase detection reaction ("LDR") coupled to polymerase chain reaction ("PCR"); (2) primary PCR coupled to secondary PCR coupled to LDR; and (3) primary PCR coupled to secondary PCR. Each of these combinations has particular utility for optimal detection. However, each of these combinations uses multiplex detection where oligonucleotide primers from an early phase of the assay system contains sequences that are utilized a later phase of the assay system.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples. Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of LDR coupled with PCR for nucleic acid detection. Barany et al., U.S. Pat. Nos. 7,556,924 and 6,858,412, describe the use of precircle probes (also called "padlock probes" or "multi-inversion probes") with coupled LDR and PCR for nucleic acid detection. Barany et al., U.S. Pat. Nos. 7,807,431, 7,709,201, and 7,198,814 describe the use of combined endonuclease cleavage and ligation reactions for the detection of nucleic acid sequences. Willis et al., U.S. Pat. Nos. 7,700,323 and 6,858,412, describe the use of precircle probes in multiplexed nucleic acid amplification, detection and genotyping. Ronaghi et al., U.S. Pat. No. 7,622,281 describes amplification techniques for labeling and amplifying a nucleic acid using an adapter comprising a unique primer and a barcode. Exemplary processes useful for amplifying and/or detecting selected nucleic acid regions include but are not limited to the methods described herein, each of which are incorporated by reference in their entirety for purposes of teaching various elements that can be used in the methods of the invention.

In addition to the various amplification techniques, numerous methods of sequence determination are compatible with the methods of the inventions. Preferably, such methods include "next generation" methods of sequencing. Exemplary methods for sequence determination include, but are not limited to, hybridization-based methods, such as disclosed in Drmanac, U.S. Pat. Nos. 6,864,052, 6,309,824, 6,401,267 and U.S. Pub. No. 2005/0191656, all of which are incorporated by reference; sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, PNAS, 100: 414-19 (2003); pyrophosphate sequencing as described in Ronaghi et al., U.S. Pat. Nos. 7,648,824, 7,459,311, 6,828,100 and 6,210,891; and ligation-based sequencing determination methods, e.g., Drmanac et al., U.S. Pub. No. 2010/0105052, and Church et al, U.S. Pub. Nos. 2007/0207482 and 2009/0018024.

Sequencing may be performed using any suitable sequencing apparatus capable of parallel sequencing at high orders of multiplexing such as the MiSeq (Illumina), Ion PGM™ (Life Technologies), Ion Torrent™ (Life Technologies), HiSeq 2000 (Illumina), HiSeq 2500 (Illumina), 454 platform (Roche), Illumina Genome Analyzer (Illumina), SOLiD System (Applied Biosystems), real-time SMRT™ technology (Pacific Biosciences) and suitable nanopore and/or nanochannel sequencers.

Alternatively, selected nucleic acid regions can be selected and/or identified using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al., *Molecular Cloning: A Laboratory Manual* (2nd Ed. Cold Spring Harbor, N.Y., 1989); Berger and Kimmel, *Methods in Enzymology*, Vol. 152; *Guide to Molecular Cloning Techniques* (Academic Press, Inc., San Diego, Calif., 1987); and Young and Davis, PNAS, 80:1194 (1983). Methods and apparatus for carrying out repeated and controlled hybridization reactions have been described in, e.g., U.S. Pat. Nos. 5,871,928, 5,874,219, 6,045,996, 6,386,749 and 6,391,623.

The present invention also contemplates signal detection of hybridization between ligands in certain preferred aspects; see U.S. Pat. Nos. 5,143,854, 5,578,832, 5,631,734, 5,834,758, 5,936,324, 5,981,956, 6,025,601, 6,141,096, 6,185,030, 6,201,639, 6,218,803 and 6,225,625, in U.S. Ser. No. 60/364,731 and in PCT Application PCT/US99/06097 (published as WO99/47964).

Methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639, 6,218,803 and 6,225,625, in U.S. Ser. No. 60/364,731 and in PCT Application PCT/US99/06097 (published as WO99/47964).

Figure 3:
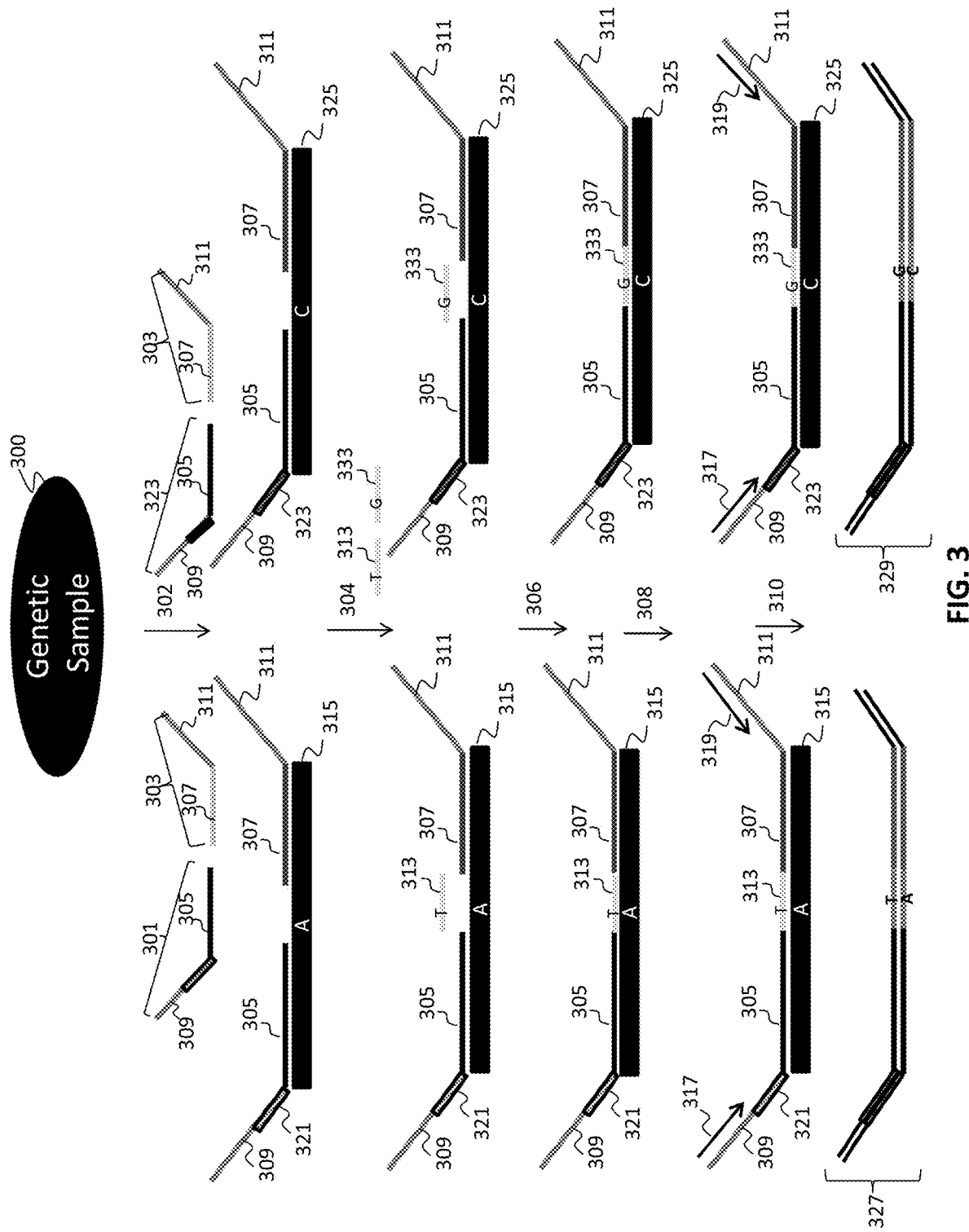
FIG. 3 illustrates an alternative multiplexed assay system for detection of two or more selected nucleic acid regions.

In FIG. 3, two sets of fixed sequence oligonucleotides are used that comprise substantially the same sequence-specific regions 305, 307 but that comprise different indices, 321, 323. The ligation reactions are carried out with material from the same genetic sample 300, but in separate tubes with the different allele-specific oligonucleotide sets. The bridging oligonucleotides 313, 333 corresponding to the two possible SNPs in the selected nucleic acid region 313, 333 are used to detect of the selected nucleic acid region in each ligation reaction. Two allele indices 321, 323 that are indicative of the SNPs can be used to identify the amplification products so that sequence determination of the actual sequence of the nucleic acids of interest and SNP are not necessarily needed, although these sequences may still be determined to identify and/or provide confirmation of the allele. Each of the fixed sequence oligonucleotides comprises a region complementary to the selected nucleic acid region 305, 307, and universal primer sequences 309, 311 that are used to amplify the different selected nucleic acid regions following initial selection and/or isolation. The universal primer sequences are located at the ends of fixed sequence oligonucleotides 301, 303, and 323 flanking the indices and the regions complementary to the nucleic acid of interest, thus preserving the nucleic acid-specific sequences and the allele indices in the amplification products. The fixed sequence oligonucleotides 301, 303, 323 are introduced at step 302 to an aliquot of the genetic sample 300 and allowed to hybridize to selected nucleic acid regions 315 or 325. Following hybridization, unhybridized fixed sequence oligonucleotides preferably are separated from the remainder of the genetic sample (not shown).

The bridging oligos corresponding to an A/T SNP 313 or a G/C SNP 333 are introduced at step 304 and allowed to bind in the region of the selected nucleic acid region 315 or 325 between the first 305 and second 307 nucleic acid-complementary regions of the fixed sequence oligonucleotides. Alternatively, the bridging oligos 313, 333 can be introduced to the sample simultaneously with the fixed sequence oligonucleotides. The bound oligonucleotides are ligated at step 306 in the reaction mixture to create a contiguous oligonucleotide spanning and complementary to the nucleic acid region of interest. Also, it should be noted that in some assays, some bridging oligonucleotides will be polymorphism-specific and some will not, as both non-polymorphic (or polymorphism agnostic) nucleic acid regions of interest and polymorphic nucleic acid regions of interest can be interrogated in a single assay.

Following ligation, the separate reactions preferably are combined for universal amplification and detection steps. Universal primers 317, 319 are introduced at step 308 to the combined reactions to amplify the ligated oligonucleotides and create at step 310 products 327, 329 that comprise the sequence of the nucleic acid region of interest representing the SNPs in the selected nucleic acid region. Products 327, 329 are detected and quantified by sequencing the products or portions of the products, through identification of the allele index, the region of the product containing the SNP from the selected nucleic acid region, or both. Preferably, the products of the methods of FIG. 3 are detected and quantified through next generation sequencing of the allele indices, thus obviating the need for determining the actual sequences of the region of the product complementary to the selected nucleic acid region or of the entire product. In other aspects, however, it may be desirable to determine the sequence of both the index and the region of the product complementary to the selected nucleic acid region, for example, to provide confirmation of the results.

In the methods of FIG. 3 (and in the methods illustrated in the other figures), an allele index has been described. However, the indices shown at 321 and 323 may be allele indices, sample indices, combined allele and sample indices, locus indices, or any other index or combination of indices described herein or otherwise used in the art.

In addition, methods may be employed where the distinguishing nucleotide is located on the fixed sequence oligonucleotides instead of a bridging oligonucleotide. Thus, in such an exemplary assay system, an allele index is associated with an allele-specific fixed sequence oligonucleotide, and the allele detection results from the sequencing of the allele index. The allele index may be embedded in either the allele-specific first sequence oligonucleotide or the second fixed sequence oligonucleotide. In specific aspects, an allele index is present on both the first and second fixed sequence oligonucleotides to detect two or more polymorphisms within the selected nucleic acid regions. The number of fixed sequence oligonucleotides used in such aspects can correspond to the number of possible alleles being assessed for a selected nucleic acid region, and sequence determination of the allele index can detect presence, amount or absence of a specific allele in the genetic sample.

Figure 4:
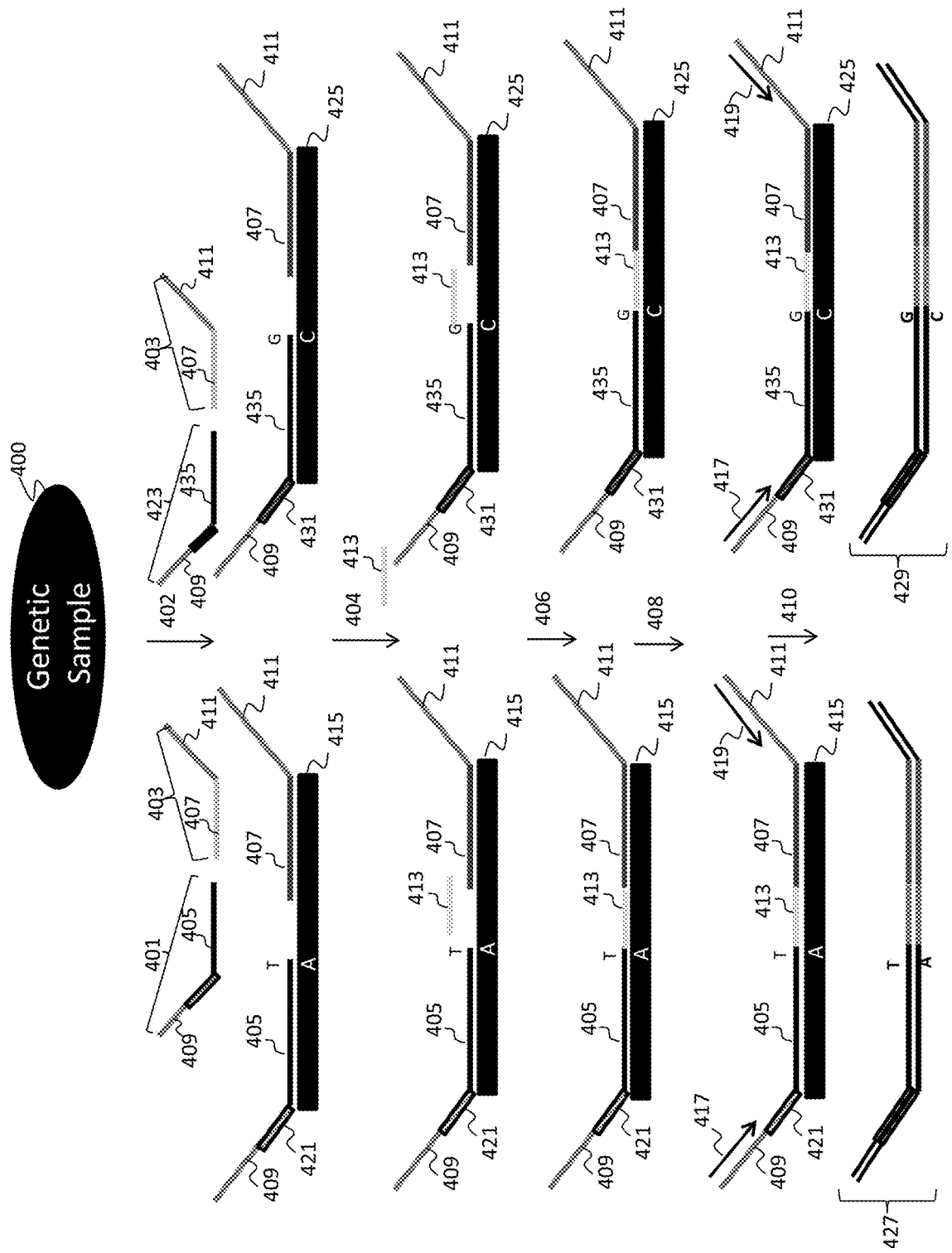
FIG. 4 illustrates yet another alternative multiplexed assay system for detection of two or more selected nucleic acid regions.

FIG. 4 illustrates this aspect of the invention. In FIG. 4, three fixed sequence oligonucleotides 401, 403 and 423 are used. Two of the fixed sequence oligonucleotides 401, 423 are allele-specific, comprising a region complementary to an allele in a nucleic acid region comprising for example an A/T or G/C SNP, respectively. Each of the allele-specific fixed sequence oligonucleotides 401, 423 also comprises a corresponding allele index 421, 431 and a universal primer sequence 409. The second fixed sequence oligonucleotide 403 has a second universal primer sequence 411, and these universal primer sequences are used to amplify the selected nucleic acid regions hybridization and ligation of the sets of oligonucleotides to the selected nucleic acid regions from the genetic sample. The universal primer sequences are located at the ends of the fixed sequence oligonucleotides 401, 403, 423 flanking the indices and regions in the fixed sequence oligonucleotides complementary to the selected nucleic acid regions of interest; thus capturing the nucleic acid-specific sequences and the indices in the products of any universal amplification methods.

The fixed sequence oligonucleotides 401, 403, 423 are introduced in step 402 to the genetic sample 400 and allowed to hybridize to selected nucleic acid regions 415, 425. Following hybridization, the unhybridized fixed sequence oligonucleotides preferably are separated from the remainder of the genetic sample (not shown). The bridging oligos 413 are introduced and allowed to hybridize to 404 to the nucleic acid 415 in the region between the first allele-specific fixed sequence oligonucleotide region 405 and the other fixed sequence oligonucleotide region 407 or to the nucleic acid 425 complementary to the region between the second allele-specific fixed sequence oligonucleotide region 435 and the other fixed sequence oligonucleotide region 407. Alternatively, the bridging oligonucleotides 413 may be introduced to the sample simultaneously with the sets of fixed sequence oligonucleotides. As stated previously in relation to FIG. 3, it should be noted that in some assays some sets of oligonucleotides will be polymorphism-specific and some will not, as both non-polymorphic (or polymorphism agnostic) nucleic acid regions of interest and polymorphic nucleic acid regions of interest can be interrogated in a single assay.

The oligonucleotides hybridized to the selected nucleic acid regions are ligated at step 406 to create a contiguous oligonucleotide spanning and complementary to the selected nucleic acid regions of interest. The ligation primarily occurs only when the allele-specific ends of the allele-specific fixed sequence oligonucleotides are complementary to the SNP in the selected nucleic acid region. Following ligation, universal primers 417, 419 are introduced to amplify at step 408 the ligated oligonucleotide to create at step 410 products 427, 429 that comprise the sequence of the nucleic acid regions of interest. These products 427, 429 are detected and quantified through sequence determination of all or a portion of the product, and in particular the region of the product containing the SNP in the selected nucleic acid region and/or the allele index. Here, the allele-specific nucleotide is shown as being at the end of the allele-specific fixed sequence oligonucleotide, yet the allele-specific nucleotide need not be so located. However, in order to make the ligation allele-specific, the allele specifying nucleotide must be close to the ligated end. Typically, the allele-specific nucleotide must be within 5 nucleotides of the ligated end. In a preferred aspect, the allele-specific nucleotide is the penultimate or ultimate (terminal) nucleotide.

Figure 5:
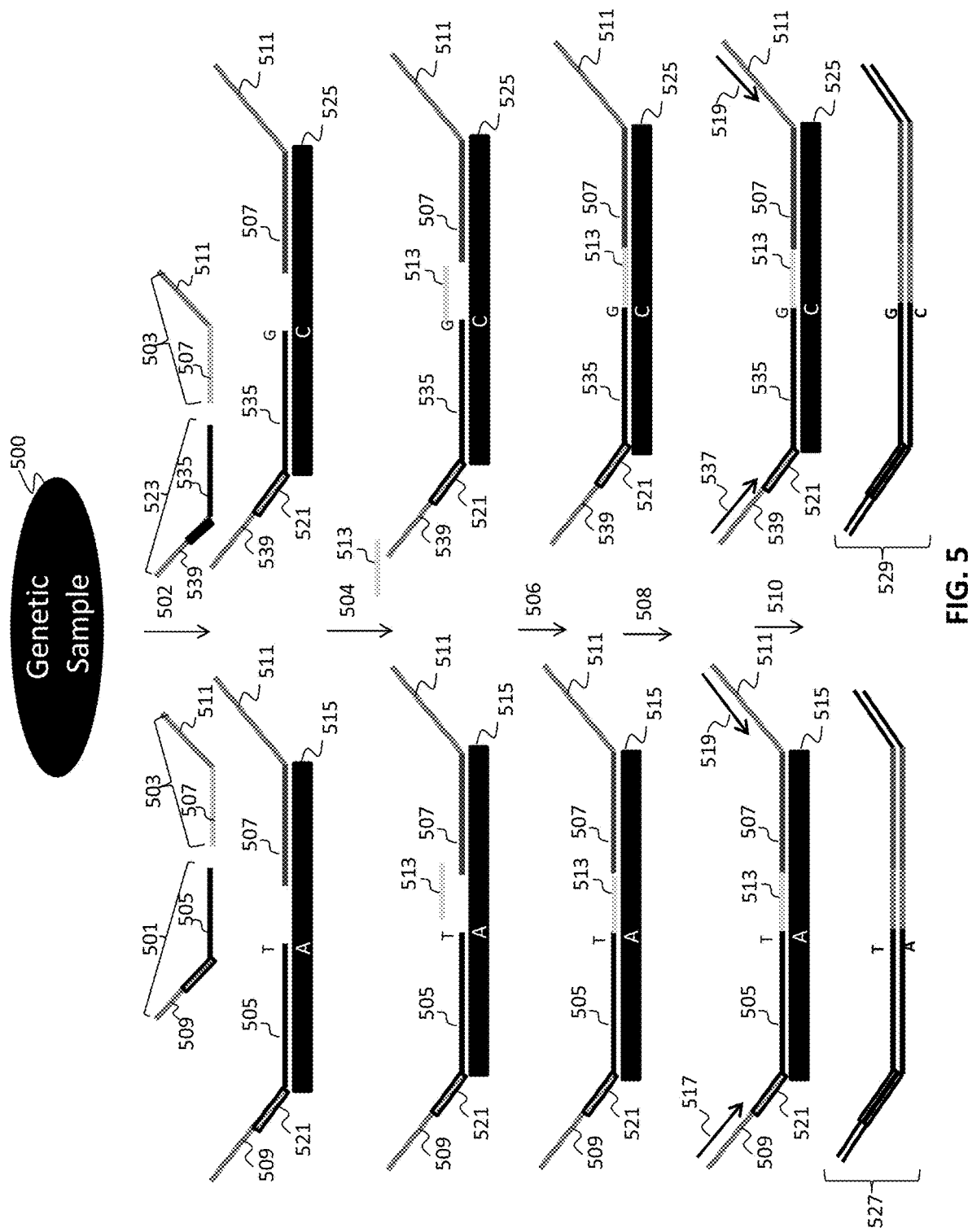
FIG. 5 illustrates yet another alternative multiplexed assay system for detection of two or more selected nucleic acid regions.

In yet another example of the assay of the present invention, allele detection results from the hybridization of a locus index to an array. Each allele is detected through an allele-specific labeling step, where each allele is labeled, e.g., with a spectrally distinct fluorescent label during the universal amplification. FIG. 5 illustrates this aspect of the invention. In FIG. 5, three fixed sequence oligonucleotides 501, 503 and 523 are used. Two of the fixed sequence oligonucleotides 501, 523 are allele-specific, and each comprises a region matching a different allele in the same selected nucleic acid region, a locus index 521 and allele-specific universal primer sequences 509, 539. The third, non-allele-specific fixed sequence oligonucleotide 503 comprises another universal primer sequence 511. The universal primer sequences are used to amplify the selected nucleic acid regions following hybridization and ligation of the oligonucleotides. Labels are incorporated into the amplification products that distinguish each allele. As in previous example, the universal primer sequences are located at the proximal ends of the fixed sequence oligonucleotides 501, 503, 523 and thus capture the allele-specific sequences and the indices in the products of any universal amplification methods. The fixed sequence oligonucleotides 501, 503, 523 are introduced in step 502 to the genetic sample 500 and allowed to specifically bind to selected nucleic acid regions 515, 525. Following hybridization, the unhybridized fixed sequence oligonucleotides preferably are separated from the remainder of the genetic sample (not shown). The bridging oligos 513 are introduced and allowed to bind at step 504 to the region of the selected nucleic acid regions 515, 525 between the first (allele-specific) 505 and second (non-allele-specific) 507 fixed sequence oligonucleotides and between the first (allele-specific) 535 and second 507 (non-allele-specific) fixed sequence oligonucleotides. Alternatively, the bridging oligos 513 may be introduced to the sample simultaneously with the fixed sequence oligonucleotides.

The bound oligonucleotides are ligated at step 506 to create a contiguous oligonucleotide spanning and complementary to the selected nucleic acid regions of interest. The ligation primarily occurs when the allele-specific ends match. Following ligation, universal primers 517, 519, 537 are introduced to amplify at step 508 the ligated oligonucleotide to create at step 510 products 527, 529 that comprise the sequence of the selected nucleic acid region of interest. Universal primers 517 and 537 have spectrally distinct fluorescent labels such that the allele-specific information is captured and can be read out through these fluorescent labels. Products 527, 529 are detected and quantified through hybridization of the locus index 521 to an array and imaging. As described in relation to FIG. 4, it is important to note that the ligation 506 is preferably allele-specific; thus, the distinguishing nucleotide is located at least 5 nucleotides from the end of the allele-specific fixed sequence oligonucleotide and preferably is located as the penultimate or ultimate nucleotide. The example shown in FIG. 5 where a locus index is used for hybridization to an array can be used in any of the various methods described herein such as methods where the fixed sequence oligonucleotides and bridging oligonucleotide do not hybridize adjacently and a polymerase and dNTPs are used to close the "gap" between oligonucleotides followed by ligation. Similarly, the locus index/hybridization methods may be used in protocols where only fixed sequence oligonucleotides are used—that is, no bridging oligonucleotide is present—and where the fixed sequence oligonucleotides hybridize adjacently and are joined by ligation or where the fixed sequence oligonucleotides hybridize with a gap between them and are joined using a polymerase and dNTPs followed by ligation.

In an alternative aspect, an allele index is present on both the first and second fixed sequence oligonucleotides to detect polymorphisms at the ends of each fixed sequence oligonucleotide using a corresponding spectrally distinct fluorescent label for each fixed sequence oligonucleotide for a given allele. In this method, the number of fixed sequence oligonucleotides corresponds to the number of possible alleles being assessed for a selected nucleic acid region. In the above figures and examples, the fixed sequence oligonucleotides are represented as two distinct oligonucleotides. In another aspect, the fixed sequence oligonucleotides may be opposite ends of the same oligonucleotide (see, e.g., FIG. 7, supra).

Figure 6:
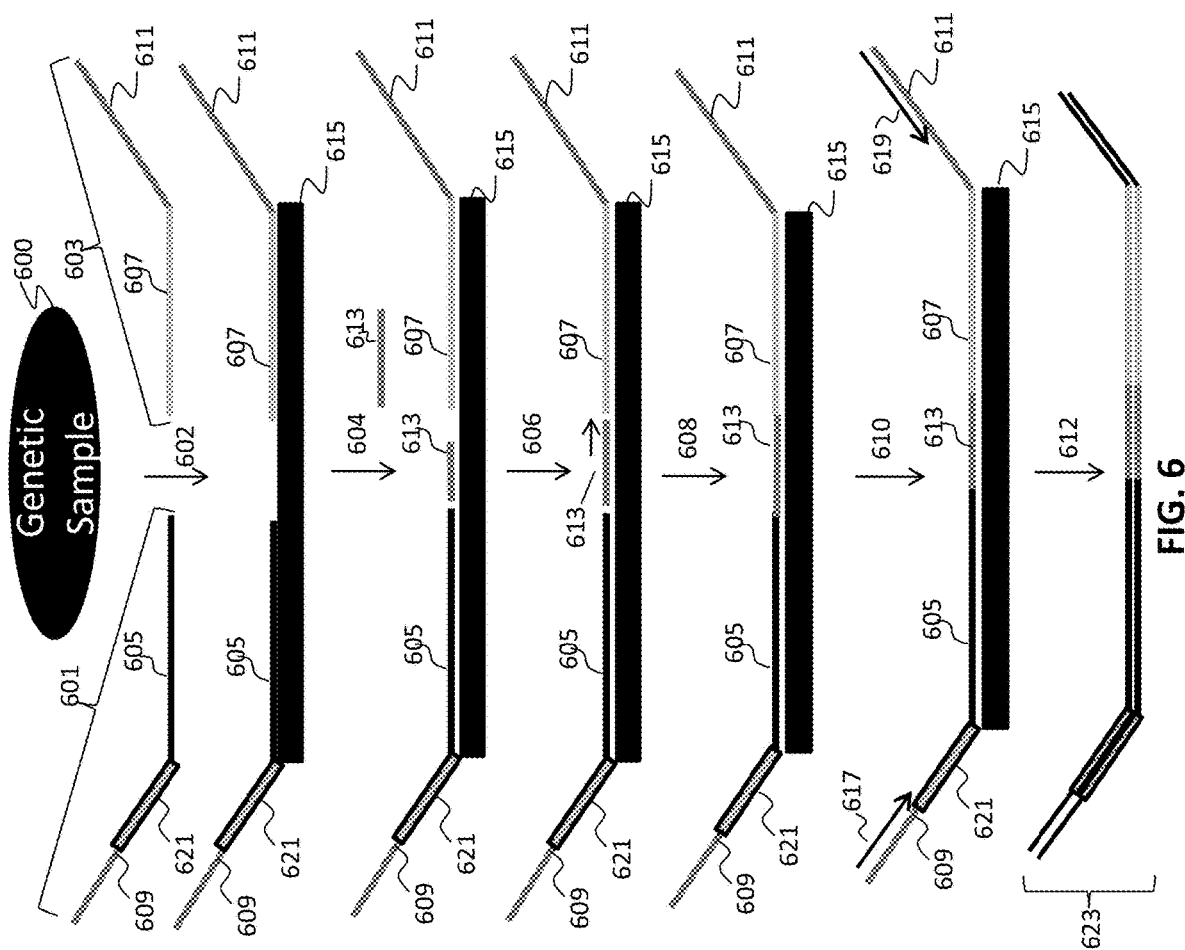
FIG. 6 illustrates yet another alternative multiplexed assay system for detection of selected nucleic acid regions.

In the aspects described above, the bridging oligos used hybridize to regions of the nucleic acid of interest adjacent to the regions complementary to the fixed sequence oligonucleotides, so that when the fixed sequence and bridging oligo(s) specifically hybridize they are directly adjacent to one another for ligation. In other aspects, however, the bridging oligo hybridizes to a region that is not directly adjacent to the region complementary to one or both of the fixed sequence oligos, and an intermediate step requiring extension of one or more of the oligos is necessary prior to ligation. For example, as illustrated in FIG. 6, each set of oligonucleotides preferably contains two fixed sequence oligonucleotides 601, 603 and one or more bridging oligonucleotides 613. Each of the fixed sequence oligonucleotides comprises a region complementary to the selected nucleic acid region 605, 607, and preferably universal primer sequences 609, 611; that is, oligonucleotide regions complementary to universal primers. The universal primer sequences 609, 611 are located at or near the ends of the fixed sequence oligonucleotides 601, 603, and thus capture the nucleic acid-specific sequences in the products of any universal amplification methods.

The fixed sequence oligonucleotides 601, 603 are introduced at step 602 to the genetic sample 600 and allowed to specifically bind to complementary portions of selected nucleic acid region of interest 615. Following hybridization, the unhybridized fixed sequence oligonucleotides preferably are separated from the remainder of the genetic sample (not shown). The bridging oligonucleotide is then introduced and allowed to bind at step 604 to the region of the selected nucleic acid region 615 between the first 601 and second 603 fixed sequence oligonucleotides. Alternatively, the bridging oligonucleotide can be introduced to the sample simultaneously with the fixed sequence oligonucleotides. In the exemplary aspect shown here, the bridging oligonucleotide hybridizes to a region directly adjacent to the first fixed sequence oligonucleotide region 605, but is separated by one or more nucleotides from the complementary region of the second fixed sequence oligonucleotide 607. Following hybridization of the fixed sequence and bridging oligonucleotides, the bridging oligonucleotide 613 is extended at step 606, e.g., using a polymerase and dNTPs, to fill the gap between the bridging oligonucleotide 613 and the second fixed sequence oligonucleotide 603. Following extension, the hybridized oligonucleotides are ligated at step 608 to create a contiguous oligonucleotide spanning and complementary to the selected nucleic acid region of interest 615. After ligation, universal primers 617, 619 are introduced at step 610 to amplify the ligated oligonucleotide to create at step 612 products 623 that comprise the sequence of the nucleic acid region of interest. These products 623 are isolated, detected, and quantified to provide information on the presence and amount of the selected nucleic acid regions in the genetic sample. Preferably, the products are detected and quantified through next generation sequencing of an allele index 621, or, alternatively, sequence determination of the portion of the amplification product complementary to the selected nucleic acid of interest 615 within the amplification product 623.

Figure 7:
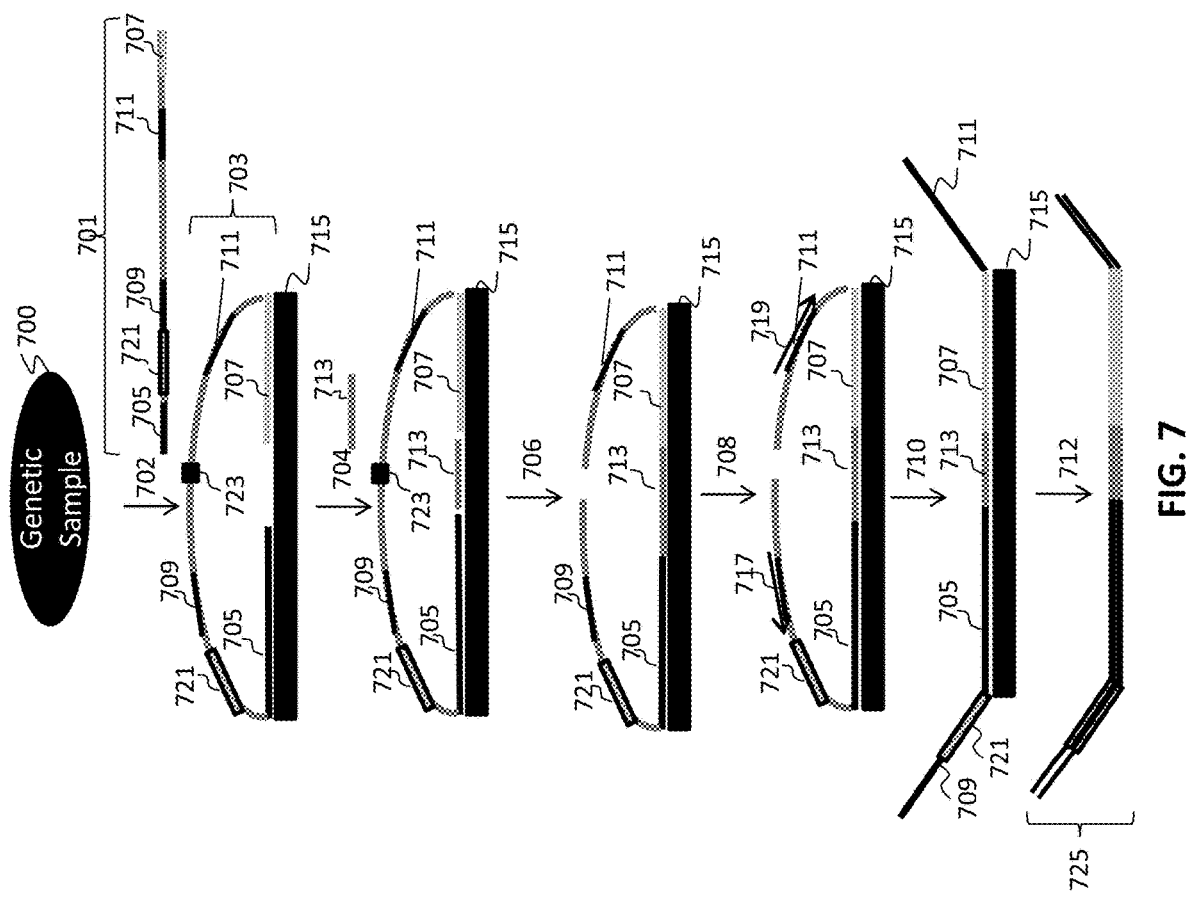
FIG. 7 illustrates yet another alternative multiplexed assay system for detection of selected nucleic acid regions.

FIG. 7 illustrates how the fixed sequence oligonucleotides may be a part of the same molecule. In specific aspects, the single fixed sequence oligonucleotide 701 is complementary to the selected nucleic acid region 715 on both ends. When this single fixed sequence oligonucleotide 701 hybridizes to the selected nucleic acid region 715, it forms a pre-circle oligonucleotide 703 where the ends are separated by several nucleotides. The bridging oligonucleotide 713 then binds between the complementary regions 705, 707 of the pre-circle oligonucleotide 703 to fill this gap. The oligonucleotide regions 705, 707 of the pre-circle oligonucleotide 703 bound to the genetic sample 715 are then ligated together with the bridging oligonucleotide 713, forming a complete circle. As with other methods exemplified herein, use of a bridging oligonucleotide is not necessary, and in such embodiments the fixed sequence oligonucleotides may hybridize adjacently, or a polymerase and dNTPs can be used to fill a gap if the fixed sequence oligonucleotides do not hybridize adjacently. The circular template is preferably the cleaved and amplified using one or more of the universal primer sites. In specific aspects, a single universal primer region is used to replicate the template using techniques such as rolling circle replication, as disclosed in Lizardi et al., U.S. Pat. No. 6,558,928.

As illustrated in FIG. 7, the fixed sequence oligonucleotide has two universal priming sites 709, 711 on the circular template and optionally one or more indices 721 between the ends of the construct that are complementary to the selected nucleic acid region. Shown here, a cleavage site 723 exists between the two universal priming sites. Construct 701 is introduced to the genetic sample at step 702, allowed to hybridize to the selected nucleic acid region of interest, and at step 704 the bridging oligonucleotide is introduced and allowed to hybridize to the selected nucleic acid region. The construct is then circularized through ligation at step 706 to the bridging oligo 713, and a nuclease can be used to remove all or most uncircularized oligonucleotides. After removal of the uncircularized oligonucleotides, the circularized oligonucleotide is cleaved, preserving and in some aspects exposing the universal priming sites 709, 711. Universal primers 717, 719 are added at step 708 and a universal amplification occurs 710 to create 712 products 725 that comprise the sequence of the selected nucleic acid region of interest. The products 725 are detected and quantified through, e.g., next generation sequencing of the portion of the produce complementary to the selected nucleic acid region or alternatively the index, which obviates the need for sequencing the entire construct. In other aspects, however, it is desirable to determine the product comprising sequences of both the index and the selected nucleic acid region, for example, to provide internal confirmation of the results or where the index provides sample information and is not informative of the selected nucleic acid region. As mentioned above, this single fixed sequence oligonucleotide methodology may be applied to any of the examples in FIGS. 2-7. Also again it should be noted that in some assays, some sets of oligonucleotides will be polymorphism-specific and some will not, as both non-polymorphic (or polymorphism agnostic) nucleic acid regions of interest and polymorphic nucleic acid regions of interest can be interrogated in a single assay.

Use of Indices in the Methods of the Invention

As described in relation to FIGS. 2-7, above, in certain aspects the fixed sequence oligonucleotides in a set comprise one or more indexes or indices that, e.g., identify the selected nucleic acid regions (a locus index), SNPs within a selected nucleic acid region (an allele index) and/or a particular sample being analyzed (a sample index). For example, the detection of the one or more locus indices can serve as a surrogate for detection of the entire selected nucleic acid region as described below, or detection of an index may serve as confirmation of the presence of a particular selected nucleic acid region if both the sequence of the index and the sequence of the oligonucleotide product complementary to the nucleic acid region itself are determined. Indices preferably are associated with the selected nucleic acid regions during the selective amplification step using primers that comprise both the index and a region that specifically hybridizes to the selected nucleic acid region (that is, selected nucleic acid region-specific sequences).

Indices are typically non-complementary, unique sequences used within an amplification primer to provide information relevant to the selected nucleic acid region that is isolated and/or amplified using the primer. The order and placement of indices, as well as the length of indices, can vary, and indices can be used in various combinations. Alternatively, the indices and/or universal amplification sequences can be added to the selectively-amplified selected nucleic acid regions following initial selective amplification using ligation of adaptors comprising these sequences. The advantage of employing indices is that the presence (and ultimately the quantity or frequency) of the selected nucleic acid regions can be obtained without the need to sequence the entire length of the selected nucleic acid regions, although in certain aspects it may be desirable to do so. Generally, however, the ability to identify and quantify a selected nucleic acid region through identification of one or more indices will decrease the length of sequencing required, particularly if the index sequence is captured at the 3' or 5' end of the isolated selected nucleic acid region proximal to where a sequencing primer may be located. Use of indices as a surrogate for identification of selected nucleic acid regions also may reduce sequencing errors since longer sequencing reads are more prone to the introduction or error. Also, as described above in relation to FIG. 5, the locus index—in conjunction with, e.g., fluorescent labels—may be used to identify and quantify the selected nucleic acid regions by hybridization to an array.

In one example of an index, the primers used for selective amplification of the selected nucleic acid regions are designed to include a locus index between the region complementary to the selected nucleic acid regions and the universal amplification primer site. A locus index typically is unique for each selected nucleic acid region so that quantification of the number of times a particular locus index occurs in a sample can be related to the relative number of copies of the corresponding single nucleic acid region and the particular chromosome containing the single nucleic acid region. Generally, the locus index is long enough to label each known single nucleic acid region uniquely. For instance, if the method uses 192 known single nucleic acid regions, there are at least 192 unique locus indexes, each uniquely identifying a single nucleic acid region from a particular locus on a chromosome. The locus indices used in the methods of the invention may be indicative of different single nucleic acid regions on a single chromosome as well as known single nucleic acid regions present on different chromosomes within a sample. The locus index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, or any other aspect of the methods.

In another example, the primers used for amplification of the selected nucleic acid regions may be designed to provide an allele index (as an alternative to a locus index) between the region complementary to the selected nucleic acid region and the universal amplification primer site. An allele index is unique for a particular allele of a selected nucleic acid region, so that quantification of the number of times a particular allele index occurs in a sample can be related to the relative number of copies of that allele, and the summation of the allelic indices for a particular selected nucleic acid region can be related to the relative number of copies of that selected nucleic acid region on the particular chromosome containing the selected nucleic acid region. In embodiments where both polymorphism-specific oligonucleotides sets and polymorphism- or SNP-agnostic oligonucleotides sets are used in a single assays, both allele and locus indices may be employed.

In yet another example, the primers used for amplification of the selected nucleic acid regions may be designed to provide an identification index between the region complementary to a selected nucleic acid region and the universal amplification primer site. In such an aspect, a sufficient number of identification indices are present to uniquely identify each amplified molecule in the sample. Identification index sequences are preferably 6 or more nucleotides in length. In a preferred aspect, the identification index is long enough to have statistical probability of labeling each molecule with a single nucleic acid region uniquely. For example, if there are 3000 copies of a particular single nucleic acid region, there are substantially more than 3000 identification indexes such that each copy of a particular single nucleic acid region is likely to be labeled with a unique identification index. As with other indices, the identification index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay.

The identification index may be combined with any other index to create one index that provides information for two properties. The identification locus may also be used to detect and quantify amplification bias that occurs downstream of the initial isolation of the selected nucleic acid regions from a sample and this data may be used to normalize the sample data.

In addition to the other indices described herein, a correction index may be employed. A correction index is a short nucleotide sequence that allows for correction of amplification, sequencing or other experimental errors including the detection of a deletion, substitution, or insertion of one or more bases during sequencing as well as nucleotide changes that may occur outside of sequencing such as oligonucleotide synthesis, amplification, or \other aspects of the assay. Correction indices may be stand-alone indices that are separate sequences, or they may be embedded within other indices to assist in confirming accuracy of the experimental techniques used, e.g., a correction index may be a subset of sequences of a locus index or an identification index.

In some aspects, indices that indicate the sample from which the selected nucleic acid regions are isolated are used to identify the source of the selected nucleic acid regions in a multiplexed assay system. In such aspects, the selected nucleic acid regions from one individual will be assigned to and associated with a particular unique sample index. The sample index can thus be used to assist in nucleic acid region identification for multiplexing of different samples in a single reaction vessel (i.e., in the case of pooling of samples), such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely. After the sequencing step is performed, the sequencing data preferably is first segregated by sample index prior to determining the frequency of each the selected nucleic acid region for each sample and prior to determining whether there is a chromosomal abnormality for each sample.

Variation Minimization within Samples

One challenge with the detection of chromosomal abnormalities in a mixed sample is that often the DNA from the cell type with the chromosomal abnormality (i.e., fetal DNA) is present in much lower abundance than the DNA from a euploid cell type (i.e., maternal DNA). In the case of a maternal sample containing fetal and maternal cell free DNA, the cell free fetal DNA as a percentage of the total cell free DNA may vary from less than one to forty percent, and most commonly is present at or below twenty percent and frequently at or below ten percent. For example, in the detection of a Y chromosome aneuploidy in the fetal DNA of such mixed maternal sample, the relative increase in Y chromosomal sequences is a multiple of the expected percentage of Y sequences if the fetus is a normal male, and thus as a percentage of the total DNA in a mixed sample where, as an example, the fetal DNA is 5% of the total, the increase in the contribution of the Y chromosome as a percentage of the total is $1/47^{th}$ of 5% (0.11% of the total percent DNA in the sample). If one is to detect this difference robustly through the methods described herein, the variation in the measurement of the Y chromosome has to be much less than the percent increase of the Y chromosome.

In some aspects, the measured quantity of one or more selected nucleic acid regions on a chromosome is normalized to account for known variation from sources such as the assay system (e.g., temperature, reagent lot differences), underlying biology of the sample (e.g., nucleic acid content), operator differences, or any other variables. Further, the data used to determine the frequency of the selected nucleic acid regions may exclude outlier data that appear to be due to experimental error, or that have elevated or depressed levels based on an idiopathic genetic bias within a particular sample. In one example, the data used for summation may exclude nucleic acid regions with a particularly elevated frequency in one or more samples. In another example, the data used for summation may exclude selected nucleic acid regions that are found in a particularly low abundance in one or more samples.

The variation between samples and/or for selected nucleic acid regions within a sample may be minimized using a combination of analytical methods. For instance, variation is lessened by using an internal reference in the assay. An example of an internal reference is the use of a chromosome present in a "normal" abundance (e.g., disomy for an autosome) to compare against the X and Y chromosomes that may be present in abnormal abundance, i.e., an aneuploidy or trace contaminant, in the same sample. While the use of a single such "normal" chromosome as a reference chromosome may be sufficient, it is preferable to use two to several autosomes as internal reference chromosomes to increase the statistical power of the quantification.

One utilization of an internal reference is to calculate a ratio of abundance of the putatively abnormal X and/or Y chromosome frequency to the abundance of autosomes in a sample, called a chromosomal ratio. In calculating the chromosomal ratio, the abundance or counts of each of the selected nucleic acid regions for each chromosome are summed together to calculate the total counts for each chromosome. The total counts for one chromosome are then divided by the total counts for a different chromosome to create a chromosomal ratio for those two chromosomes.

Alternatively, a chromosomal ratio for each chromosome may be calculated by first summing the counts of each of the selected nucleic acid regions for each chromosome, and then dividing the sum for one chromosome by the total sum for two or more chromosomes. Once calculated, the chromosomal ratio is then compared to the average chromosomal ratio from a euploid population.

The average may be the mean, median, mode or other average, with or without normalization or exclusion of outlier data. In a preferred aspect, the mean is used. In developing the data set for the chromosomal ratio from the euploid population, the normal variation of the measured chromosomes is calculated. This variation may be expressed a number of ways, most typically as the coefficient of variation, or CV. When the X chromosomal ratio from the sample is compared to the average chromosomal ratio from a euploid population, if the X chromosomal ratio for the sample falls statistically outside of the average chromosomal ratio for the euploid population, the sample contains an X chromosomal abnormality indicative of, e.g., an X aneuploidy and/or an X chromosome mosaicism. Similarly, when the Y chromosomal ratio from the sample is compared to the average chromosomal ratio from a euploid population, if the Y chromosomal ratio for the sample falls statistically outside of the average chromosomal ratio for the euploid population, the sample contains a Y chromosomal abnormality indicative of, e.g., a Y aneuploidy and/or a Y chromosome mosaicism.

The criteria for setting the statistical threshold to declare an aneuploidy depend upon the variation in the measurement of the chromosomal ratio and the acceptable false positive and false negative rates for the desired method. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is determined by summing the counts of selected nucleic acid regions by chromosome. Typically, the same number of selected nucleic acid regions for each chromosome is used.

An alternative method for generating the chromosomal ratio would be to calculate the average counts for the selected nucleic acid regions for each chromosome or chromosomal region. The average may be any estimate of the mean, median or mode, although typically an average is used. The average may be the mean of all counts or some variation such as a trimmed or weighted average. Once the average counts for each chromosome have been calculated, the average counts for each chromosome may be divided by the other to obtain a chromosomal ratio between two chromosomes, the average counts for each chromosome may be divided by the sum of the averages for all measured chromosomes to obtain a chromosomal ratio for each chromosome as described above. As highlighted above, the ability to detect an X chromosome, X chromosome frequency, Y chromosome or Y chromosomal frequency in a maternal sample where the fetal DNA is in low relative abundance depends greatly on the variation in the measurements of different selected nucleic acid regions in the assay. Numerous analytical methods can be used that reduce this variation and thus improve the sensitivity of this method to detect aneuploidy.

One method for reducing variability of the assay is to increase the number of selected nucleic acid regions used to calculate the abundance of the chromosomes. In general, if the measured variation of a single selected nucleic acid region of a chromosome is B % and C different selected nucleic acid regions are measured on the same chromosome, the variation of the measurement of the chromosomal abundance calculated by summing or averaging the abundance of each selected nucleic acid region on that chromosome will be approximately B % divided by $C^{1/2}$. Stated differently, the variation of the measurement of the chromosome abundance would be approximately the average variation of the measurement of each selected nucleic acid region's abundance divided by the square root of the number of selected nucleic acid regions.

In a preferred aspect of this invention, the number of selected nucleic acid regions measured for each chromosome (the X chromosome, the Y chromosome and the one or more autosomes) is at least 8. In another preferred aspect of this invention the number of selected nucleic acid regions measured for each chromosome is at least 24. In yet another preferred aspect of this invention, the number of selected nucleic acid regions measured for each chromosome is at least 32. In another preferred aspect of this invention, the number of selected nucleic acid regions measured for each chromosome is at least 100. In another preferred aspect of this invention the number of selected nucleic acid regions measured for each chromosome is at least 200. There is an increased incremental cost in measuring each selected nucleic acid region and thus it is important to minimize the number of selected nucleic acid regions while still generating statistically robust data. In a preferred aspect of this invention, the number of selected nucleic acid regions measured for each chromosome is less than 2000. In a preferred aspect of this invention, the number of selected nucleic acid regions measured for each chromosome is less than 1000. In a most preferred aspect of this invention, the number of selected nucleic acid regions measured for each chromosome is at least 32 and less than 1000.

In one aspect, following the measurement of abundance for each selected nucleic acid region, a subset of the selected nucleic acid regions may be used to determine the presence or absence of an X or Y chromosomal abnormality. There are many standard methods for choosing the subset of selected nucleic acid regions, including exclusion, where the selected nucleic acid regions with detected levels below and/or above a certain percentile are discarded from the analysis. In one aspect, the percentile may be the lowest and highest 5% as measured by frequency. In another aspect, the percentile to be discarded may be the lowest and highest 10% as measured by frequency. In another aspect, the percentile to be discarded may be the lowest and highest 25% as measured by frequency.

Another method for choosing a subset of selected nucleic acid regions include the elimination of regions that fall outside of some statistical limit. For instance, regions that fall outside of one or more standard deviations of the mean abundance may be removed from the analysis. Another method for choosing the subset of selected nucleic acid regions may be to compare the relative abundance of a selected nucleic acid region to the expected abundance of the same selected nucleic acid region in a healthy population and discard any selected nucleic acid regions that fail the expectation test. To further minimize the variation in the assay, the number of times each selected nucleic acid region is measured may be increased. As discussed, in contrast to the random methods of detecting X and Y chromosome frequency abnormalities where the genome is measured on average less than once, the methods of the present invention intentionally measure each selected nucleic acid region multiple times. In general, when counting events, the variation in the counting is determined by Poisson statistics, and the counting variation is typically equal to one divided by the square root of the number of counts. In a preferred aspect of the invention, the selected nucleic acid regions are each measured on average at least 5 times. In a certain aspect to the invention, the selected nucleic acid regions are each measured on average at least 10, 50 or 100 times. In a certain aspect to the invention, the selected nucleic acid regions are each measured on average at least 250 times. In a certain aspect to the invention, the selected nucleic acid regions are each measured on average at least 500 times. In a certain aspect to the invention, the selected nucleic acid regions are each measured on average at least 1000 times or at least 5,000 or at least 10,000 times.

In another aspect, subsets of selected nucleic acid regions can be chosen randomly using sufficient numbers to yield a statistically significant result in determining whether a chromosomal abnormality exists. Multiple analyses of different subsets of selected nucleic acid regions can be performed within a maternal sample to yield more statistical power. In this example, it may or may not be necessary to remove or eliminate any selected nucleic acid regions prior to the random analysis. For example, if there are 100 selected nucleic acid regions for the Y chromosome and 100 selected nucleic acid regions for, e.g., chromosome 2, a series of analyses could be performed that evaluate fewer than 100 regions for each of the chromosomes.

Sequence counts also can be normalized by systematically removing sample and assay biases by using median polish on log-transformed counts. A metric can be computed for each sample as the mean of counts for a selected nucleic acid region divided by the sum of the mean of counts for selected nucleic acid regions on a particular chromosome and the mean of courts for the selected nucleic acid regions on a different chromosome. A standard Z test of proportions may be used to compute Z statistics:

$$Z_j = \frac{p_j - p_0}{\sqrt{\frac{p_j(1 - p_j)}{n_j}}}$$

where $p_j$ is the observed proportion for a given chromosome of interest in a given sample j, $p_0$ is the expected proportion for the given test chromosome calculated as the median $p_j$, and nj is the denominator of the proportion metric. Z statistic standardization may be performed using iterative censoring. At each iteration, the samples falling outside of, e.g., three median absolute deviations are removed. After ten iterations, mean and standard deviation were calculated using only the uncensored samples. All samples are then standardized against this mean and standard deviation. The Kolmogorov-Smirnov test (see Conover, *Practical Nonparametric Statistics*, pp. 295-301 (John Wiley & Sons, New York, N.Y., 1971)) and Shapiro-Wilk's test (see Royston, Applied Statistics, 31:115-124 (1982)) may be used to test for the normality of the euploid samples' Z statistics.

In addition to the methods above for reducing variation in the assay, other analytical techniques, many of which are described earlier in this application, may be used in combination. For example, the variation in the assay may be reduced when all of the selected nucleic acid regions for each sample are interrogated in a single reaction in a single vessel. Similarly, the variation in the assay may be reduced when a universal amplification system is used. Furthermore, the variation of the assay may be reduced when the number of cycles of amplification is limited.

Determination of Fetal DNA Content in Maternal Sample

Determining the percentage of fetal DNA in a maternal sample increases the accuracy of the frequency calculations for the selected nucleic acid regions, as knowledge of the fetal contribution provides important information on the expected statistical presence of the selected nucleic acid regions from the X and Y chromosomes. Taking percent fetal into account is particularly important in circumstances where the level of fetal DNA in a maternal sample is low, as the percent fetal contribution is used to determine the quantitative statistical significance in the X and Y chromosomal sequences in the sample. Taking percent fetal into account is important when assessing the presence of an X chromosomal aneuploidy, Y chromosomal aneuploidy or sex chromosome mosaicism and/or determining whether there is sample contamination.

The relative maternal contribution of maternal DNA at an allele of interest can be compared to the non-maternal contribution at that allele to determine approximate fetal DNA concentration in the sample. In preferred aspects, the relative quantity of solely paternally-derived sequences, e.g., paternally-specific polymorphisms on autosomes, are used to determine the relative concentration of fetal DNA in a maternal sample. Another exemplary approach to determining the percent fetal contribution in a maternal sample is through the analysis of DNA fragments with different patterns of DNA methylation between fetal and maternal DNA.

Because X and Y chromosome sequences are typically not used to calculate percent fetal in the present methods, determination of fetal polymorphisms requires targeted SNP and/or mutation analysis to identify the presence of fetal DNA in a maternal sample. In each maternally-derived sample, the DNA from a fetus will have approximately 50% of its loci inherited from the mother and 50% of the loci inherited from the father. Determining the loci contributed to the fetus from the paternal source allows for the estimation of fetal DNA in a maternal sample, and thus provides information used to calculate the statistically significant differences in chromosomal frequencies for chromosomes of interest. In some aspects, the use of prior genotyping of the father and mother can be performed. For example, the parents may have undergone genotype determination for identification of disease markers, e.g., determination of the genotype for disorders such as cystic fibrosis, muscular dystrophy, spinal muscular atrophy or even the status of the RhD gene may be determined. If so, the difference in polymorphisms, copy number variants or mutations can be used to determine the percentage fetal contribution in a maternal sample.

In an alternative preferred aspect, the percent fetal cell free DNA in a maternal sample can be quantified using multiplexed SNP detection without prior knowledge of the maternal or paternal genotype. In this aspect, selected polymorphic nucleic acid regions with one or more known SNPs in each region are used. In a preferred aspect, the selected polymorphic nucleic acid regions are located on autosomal chromosomes that are unlikely to be aneuploid, e.g., Chromosome 6. Also in a preferred aspect, selected polymorphic nucleic acid regions are amplified in one reaction in one vessel. Each allele of the selected polymorphic nucleic acid regions in the maternal sample is determined and quantified using, e.g., high throughput sequencing. Following sequence determination, loci are identified where the maternal and fetal genotypes are different, e.g., the maternal genotype is homozygous and the fetal genotype is heterozygous. Paternally-inherited sequences can be identified by detected polymorphisms that occur at a low but statistically-relevant frequency. Identification is accomplished by observing a high relative frequency of one allele (>60%) and a low relative frequency (<20% and >0.15%) of the other allele for a particular selected nucleic acid region. The use of multiple loci is particularly advantageous as it reduces the amount of variation in the measurement of the abundance of the alleles. All or a subset of the loci that meet this requirement are used to determine fetal concentration through statistical analysis.

In one aspect, fetal concentration is determined by summing the low frequency alleles from two or more loci together, dividing by the sum of the high and low frequency alleles and multiplying by two. In another aspect, the percent fetal cell free DNA is determined by averaging the low frequency alleles from two or more loci, dividing by the average of the high and low frequency alleles and multiplying by two.

For many alleles, maternal and fetal sequences may be homozygous and identical, and as this information does not distinguish between maternal and fetal DNA, it is not useful in the determination of percent fetal DNA in a maternal sample. The present methods utilize allelic information where there is a difference between the fetal and maternal DNA (e.g., a fetal allele containing at least one allele that differs from the maternal allele) in calculations of percent fetal. Data pertaining to allelic regions that are the same for the maternal and fetal DNA are thus not selected for analysis, or are removed from the pertinent data prior to determination of percentage fetal DNA so as not to swamp out the useful data. Exemplary methods for quantifying fetal DNA in maternal plasma can be found, e.g., in Chu et al., Prenat Diagn, 30:1226-29 (2010), which is incorporated herein by reference.

In one aspect, selected nucleic acid regions may be excluded if the amount or frequency of the region appears to be an outlier due to experimental error or from idiopathic genetic bias within a particular sample. In another aspect, selected nucleic acids may undergo statistical or mathematical adjustment such as normalization, standardization, clustering, or transformation prior to summation or averaging, e.g., as known in the art or as described supra. In another aspect, selected nucleic acids may undergo both normalization and data experimental error exclusion prior to summation or averaging. In a preferred aspect, 12 or more loci are used for the analysis. In another preferred aspect, 24 or more loci are used for the analysis. In another preferred aspect, 32 or more loci, 48 or more loci, 72 or more loci, 96 or more loci, 100 or more loci, or 200 or more loci are used for the analysis.

In one preferred aspect, the percentage fetal contribution in a maternal sample can be quantified using tandem SNP detection in the maternal and fetal alleles. Techniques for identifying tandem SNPs in DNA extracted from a maternal sample are disclosed in Mitchell et al, U.S. Pat. No. 7,799,531 and U.S. Ser. Nos. 12/581,070; 12/581,083; 12/689,924 and 12/850,588. These references describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

In yet another alternative, certain genes have been identified as having epigenetic differences between the maternal and fetal gene copies, and such genes are candidate loci for fetal DNA markers in a maternal sample. See, e.g., Chim, et al., PNAS USA, 102:14753-58 (2005). These loci, which may be methylated in the fetal DNA but unmethylated in maternal DNA (or vice versa), can be readily detected with high specificity by use of methylation-specific PCR (MSP) even when such fetal DNA molecules were present among an excess of background plasma DNA of maternal origin. The comparison of methylated and unmethylated amplification products in a maternal sample can be used to quantify the percent fetal DNA contribution to the maternal sample by calculating the epigenetic allelic ratio for one or more of such sequences known to be differentially regulated by methylation in the fetal DNA as compared to maternal DNA.

To determine methylation status of nucleic acids in a maternal sample, the nucleic acids of the sample are subjected to bisulfite conversion of the samples and then subjected to MSP, followed by allele-specific primer extension. Conventional methods for such bisulphite conversion include, but are not limited to, use of commercially available kits such as the Methylamp™ DNA Modification Kit (Epigentek, Brooklyn, N.Y.). Allelic frequencies and ratios can be directly calculated and exported from the data to determine the relative percentage of fetal DNA in the maternal sample.

Use of Percent Fetal Cell Free DNA in X and Y Chromosome Frequency Analysis

Once percent fetal cell free DNA has been calculated, this data is combined with methods for detection and quantification of X and Y chromosome sequences to determine the likelihood that a fetus may be female, male, aneuploid for the X chromosome, aneuploid for the Y chromosome, an X chromosome mosaic, a Y chromosome mosaic. It can also be used in the determination of maternal aneuploidies, including mosaicism, or to identify whether the maternal sample being tested is contaminated.

For example, in a maternal sample that is 10% fetal DNA, each chromosome will contribute $1/46^{th}$ of 10% (or approximately 0.22%) in a euploid fetus. In a euploid male fetus, the Y chromosome will thus contribute $1/46^{th}$ of 10% (0.22%), the X chromosome will contribute $1/46^{th}$ of 10% (0.22%), and autosome pairs will contribute $2/46^{th}$ (i.e. $1/23^{rd}$) of 10% (0.44% as there are two of each autosome). Thus, in determining whether a fetus is a euploid male fetus, the frequency of Y chromosome-specific sequences in a sample that is 10% fetal should be 0.22% and the frequency of, for example, chromosome 3-specific sequences should be 0.44% since a male fetus has two chromosome 3s. In determining whether there is a Y chromosomal aneuploidy (that is, two or more Y chromosomes), the frequency of Y chromosome-specific sequences would be approximately 0.44% for two Y chromosomes and approximately 0.66% for three Y chromosomes. In determining whether a fetus may be a Y chromosome mosaic, the frequency of Y chromosome-specific sequences should be less and may be substantially less than 0.22% for an XX/XY mosaic, and the same would be true for assessing the likelihood of sample contamination of a maternal sample with nucleic acids from a female fetus contaminated by a maternal sample with nucleic acids from a male fetus. In an XY/XYY mosaic, the frequency of Y chromosome-specific sequence should be between 0.22% and 0.44%. In another example, in a maternal sample that is 5% fetal DNA, each chromosome will contribute $1/46^{th}$ of 5% (or approximately 0.11%) in a euploid fetus. In a euploid male fetus, the Y chromosome will thus contribute $1/46^{th}$ of 5% (0.11%) and autosome pairs will contribute $2/46^{th}$ or $1/23^{rd}$ of 5% (0.22% as there are two of each autosome).

In another example, in a euploid female fetus, the X chromosome will contribute $2/46^{th}$ (i.e. $1/23^{rd}$) of 10% (0.44% as there are two X chromosomes in a euploid female fetus) and autosome pairs will contribute $2/46^{th}$ or $1/23^{rd}$ of 10% (0.44% as there are two of each autosome). Thus, in determining whether a fetus is a euploid female fetus, the frequency of X chromosome-specific sequences in a sample that is 10% fetal should be 0.44% and the frequency of, for example, chromosome 3-specific sequences should be 0.44% since a female fetus has two chromosome 3s. In determining whether there is an X chromosomal aneuploidy (that is, one, three or more than three X chromosomes), the frequency of X chromosome-specific sequences would be approximately 0.22% for one X chromosome, 0.66% for three X chromosomes and approximately 0.88% for four Y chromosomes. In determining whether a fetus may be an X chromosome mosaic, the frequency of X chromosome-specific sequences should be less and may be substantially less than 0.44% for an XX/X0 mosaic or between 0.44% and 0.66% for a XX/XXX mosaic. In another example, in a maternal sample that is 5% fetal DNA, each chromosome will contribute $1/46^{th}$ of 5% (or approximately 0.11%) in a euploid fetus. In a euploid female fetus, the X chromosome will thus contribute $2/46^{th}$ or $1/23^{rd}$ of 5% (0.22%) and autosome pairs will contribute $2/46^{th}$ or $1/23^{rd}$ of 5% (0.22% as there are two of each autosome).

Figure 8:
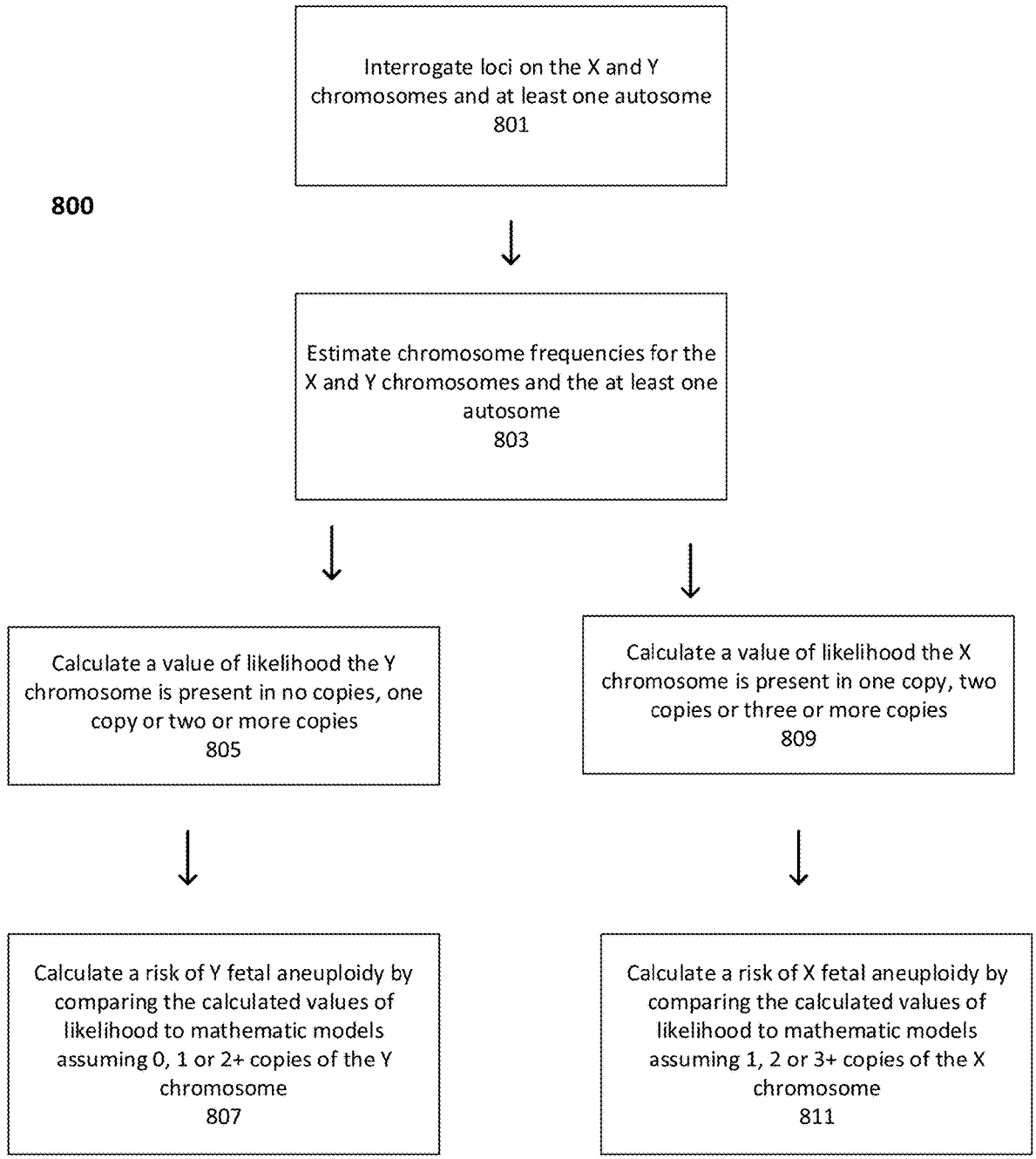
FIG. 8 is a simplified flow chart of an exemplary method for performing statistical analysis according to the present invention.

FIG. 8 is a simplified flow chart of an exemplary method 800 for performing statistical analysis according to the present invention. In step 801 of method 800, loci on the X and Y chromosomes as well as on at least one autosome are interrogated. In step 803, chromosome frequencies for each of the chromosomes interrogated in step 801 are estimated. In step 805, values of likelihood that the Y chromosome is present in no copies, one copy or two or more copies are calculated, and in step 807, a risk of Y aneuploidy is calculated by comparing the calculated values of likelihood to mathematic models assuming the Y chromosome is present in 0, 1 or 2+ copies. Similarly, in step 809, values of likelihood that the X chromosome is present in one copy, two copies or three or more copies are calculated, and in step 811, a risk of an X aneuploidy is calculated by comparing the calculated values of likelihood to mathematic models assuming the X chromosome is present in 1, 2 or 3+ copies.

Figure 9:
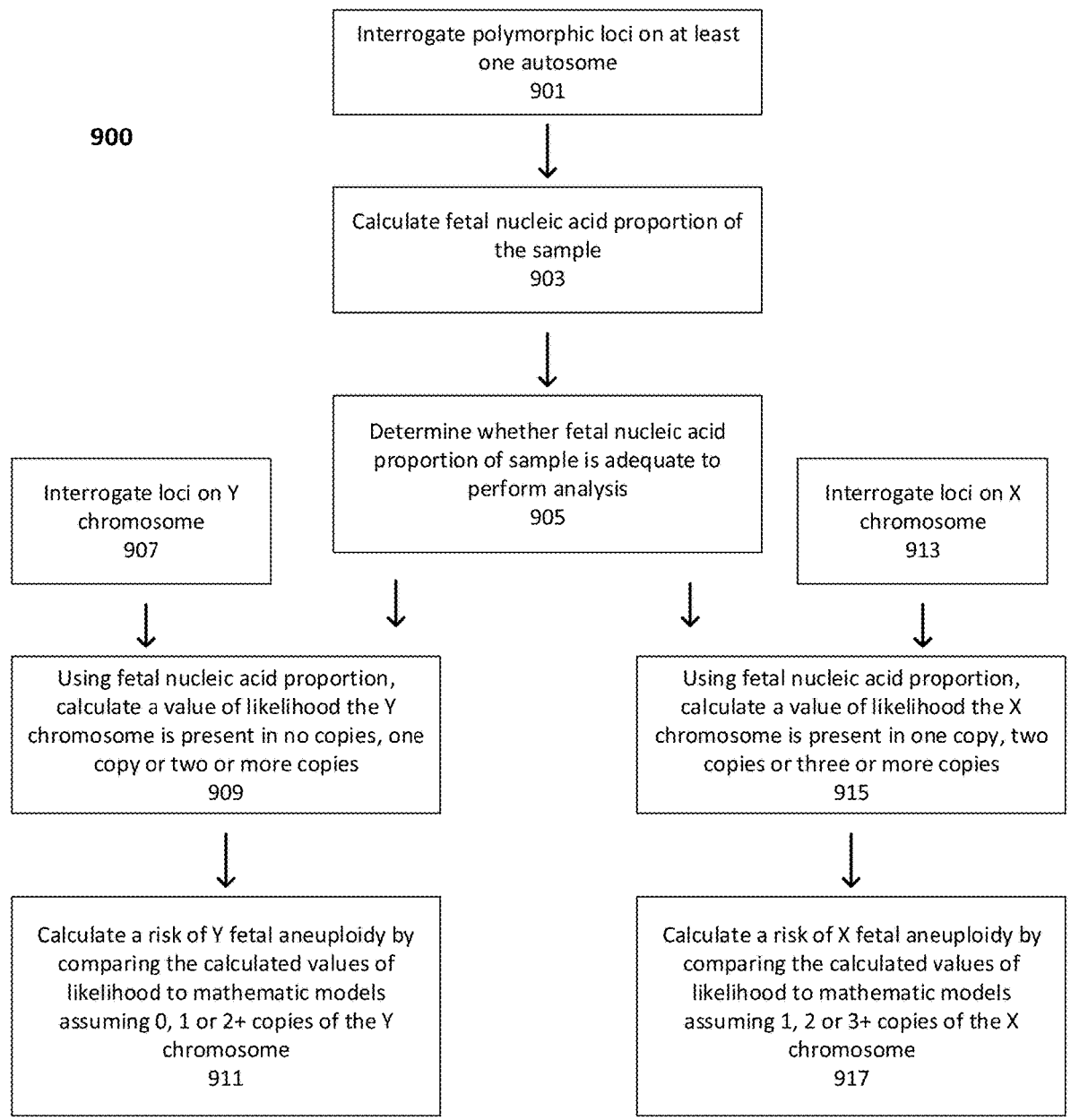
FIG. 9 is yet another simplified flow chart of an exemplary method for performing statistical analysis according to the present invention.

FIG. 9 is a simplified flow chart of another embodiment of an exemplary method 900 for performing analysis according to the present invention. In method 900, fetal proportion of the maternal sample is determined and the risk fetal X and Y aneuploides are calculated. In step 901, at least one polymorphic locus on at least one autosome is interrogated. In most embodiments of the invention, several to many polymorphic loci on at least two and often more than two autosomes will be interrogated. In step 903, the fetal nucleic acid proportion (percent fetal) of the maternal sample is calculated using the information on polymorphic loci. In step 905, a determination is made as to whether the fetal nucleic acid proportion of the maternal sample is adequate to perform further analysis. In step 907, loci (polymorphic or non-polymorphic) on the Y chromosome are interrogated. In most embodiments interrogation of loci on the Y chromosome and the X chromosome will be performed at the same time and preferably in the same vessel at the interrogation of loci on the at least one autosome. In step 909, using the calculated fetal nucleic acid proportion, the values of likelihood the Y chromosome is present in no copies, one copy or two or more copies are calculated, and in step 911, a risk of Y fetal aneuploidy is calculated by comparing the calculated values of likelihood to mathematic models assuming 0, 1 or 2+ copies of the Y chromosome. In step 913, loci (polymorphic or non-polymorphic) on the X chromosome are interrogated, and as note previously, interrogation of loci on the X chromosome and the Y chromosome will be performed at the same time and preferably in the same vessel at the interrogation of loci on the at least one autosome. In step 915, using the calculated fetal nucleic acid proportion, the values of likelihood the X chromosome is present in one copy, two copies or three or more copies are calculated, and in step 9171, a risk of X fetal aneuploidy is calculated by comparing the calculated values of likelihood to mathematic models assuming 1, 2 or 3+ copies of the X chromosome.

As mentioned above, in a preferred aspect the reactions to interrogate both the selected polymorphic nucleic acid regions for determination of percentage fetal DNA in the sample and the selected nucleic acid regions from the X and Y chromosomes are performed in a single reaction (i.e., in a single vessel). The single reaction helps to minimize the risk of contamination or bias that may be introduced during various steps in the assay system which may otherwise skew results when utilizing fetal DNA content to help determine the presence or absence of a chromosomal abnormality. Therefore, as mentioned when describing the assays, some sets of oligonucleotides used to interrogate selected nucleic acid regions will be polymorphism-specific for measuring fetal fraction and some sets of oligonucleotides used to interrogate selected nucleic acid regions will be polymorphic- or SNP-agnostic for determining fetal sex or aneuploidies of the X and Y chromosomes.

In other aspects, a selected nucleic acid region or regions may be utilized both for determination of percent fetal DNA content and detection of X and Y chromosomal abnormalities. Alleles for selected nucleic acid regions can be used to determine fetal DNA content and these same selected nucleic acid regions can then be used to detect fetal chromosomal abnormalities ignoring the allelic or SNP-specific information. Utilizing the same selected nucleic acid regions for both fetal DNA content and detection of chromosomal abnormalities further helps to minimize any bias due to experimental error or contamination.

In one embodiment, fetal source contribution in a maternal sample regardless of fetal gender is measured using autosomal SNPs (see, Sparks, et al., Am. J. Obstet & Gyn., 206:319.e1-9 (2012)). The processes utilized do not require prior knowledge of paternal genotype, as the non-maternal alleles are identified during the methods without regard to knowledge of paternal inheritance. A maximum likelihood estimate using the binomial distribution may be used to calculate the estimated fetal nucleic acid contribution across several informative loci in each maternal sample. The processes for calculation of fetal nucleic acid contribution used are described, for example, in U.S. Ser. No. 13/553,012, filed Jul. 19, 2012, which is incorporated by reference. The polymorphic regions used for determination of fetal contribution may be from chromosomes 1-12, and preferably do not target the blood group antigens.

In certain aspects, the determination of the number of Y chromosomes in the fetal DNA may be performed independently from the determination of the number of X chromosomes in the fetal DNA.

In certain aspects, the estimate of fetal contribution from the polymorphic assays is used to determine a Y chromosome fetal frequency (YFF) value. For example, in certain aspects the fetal frequency may be defined as $$YFF = 1 - \left(\frac{PF\_Poly - PF\_ChrY}{PF\_Poly}\right)$$

where PF_Poly is the estimate of percent fetal contribution from the polymorphic assays and PF_ChrY is the normalized fraction of chromosome Y counts, where PF_ChrY may be determined by, e.g., computing a ratio of median counts per chromosome Y assay and median counts per each autosome or reference chromosome assay. When the YFF value is close to zero, the fetal DNA does not likely comprise a Y chromosome. When the YFF value is close to one, the fetal DNA likely comprises a single Y chromosome. If the YFF value is close to two, the fetal DNA likely comprises two copies of the Y chromosome, and so on for additional copies of Y. In certain aspects, the YFF value is used to determine the presence of more than two copies of the Y chromosome in fetal DNA of a sample, such as three, four or five copies.

In certain aspects, the estimate of PF_Poly is used to determine an X chromosome fetal frequency (XFF) value. In certain aspects the XFF may be defined using different definitions for each potential X chromosome composition in a sample. For example, in certain aspects the X fetal probability ($\hat{p}_1$) for a sample j may be defined for fetal DNA comprising a single X chromosome as $$\hat{p}_1 = \frac{(1 - 0.5 * f_j) * p_0}{(1 - 0.5 * f_j) * p_0 + (1 - p_0)}$$

where $\hat{p}_1$ is the probability that the fetal DNA comprises a single X chromosome, $p_0$ is the reference proportion for an autosome and $f_j$ is the fetal fraction for the sample. Preferably, the fetal fraction used is the PF_Poly.

In certain aspects, the X fetal probability ($\hat{p}_2$) may be defined for fetal DNA comprising two X chromosomes as $$\hat{p}_2 = p_0$$

where $\hat{p}_2$ is the probability that the fetal DNA comprises two X chromosomes and $p_0$ is the reference proportion for a given chromosome.

In certain aspects, the X fetal probability ($\hat{p}_3$) for a sample j may be defined for fetal DNA comprising three X chromosomes as $$\hat{p}_3 = \frac{(1 + 0.5 * f_j) * p_0}{(1 + 0.5 * f_j) * p_0 + (1 - p_0)}$$

where $\hat{p}_3$ is the probability that the fetal DNA comprises three X chromosomes, $p_0$ is the reference proportion for a given chromosome and $f_j$ is the fetal fraction for the sample.

In certain aspects, the number of X chromosomes in the fetal DNA may be estimated by comparing the normalized probability value for each of $\hat{p}_1$, $\hat{p}_2$, and $\hat{p}_3$ which is, in certain embodiments, calculated by dividing the probability values calculated above by the total sum of the probability values:

$$p1 = \frac{\hat{p}_1}{\hat{p}_1 + \hat{p}_2 + \hat{p}_3}, \quad p2 = \frac{\hat{p}_2}{\hat{p}_1 + \hat{p}_2 + \hat{p}_3}, \quad p3 = \frac{\hat{p}_3}{\hat{p}_1 + \hat{p}_2 + \hat{p}_3}$$

In certain aspects, the highest normalized probability corresponds to the estimated number of X chromosomes in the fetal DNA. For example, if p2 is higher than p1 and p3, then the fetal DNA likely comprises two X chromosomes. In certain aspects, the X normalized probability value calculations are used to determine the presence of more than three copies of the X chromosome in fetal DNA of a sample, such as four, five or six copies.

Measured XFF and YFF values may be affected by variations that occur during analysis such as variation from the assay system, operator differences, or other variables. In certain aspects, a particular range of fetal difference values may be excluded as outside a baseline level of certainty for the purposes of reporting a result. In some aspects, a YFF value below zero will be considered clearly indicative that the fetus does not have a Y chromosome. In some aspects, a YFF value between zero and one does not provide the requisite level of certainty to determine the presence or absence of a Y chromosome. Therefore, in certain aspects, YFF values that fall in a certain range, such as 0 to 1, are considered outside the certainty range, such as fetal difference values in a range of 0.1 to 0.9 such as 0.2 to 0.8. Such determinations, whether or not conclusive, can be used to calculate a risk score based on the value of the probability as demonstrated above. Such risk scores can be used, e.g., to advise on clinical care of the mother and/or fetus.

Computer Implementation of the Processes of the Invention

The processes of the present invention may be implemented via a computer or computer system. For example, the raw data from the "read out" of the methods—i.e., high throughput sequencing of amplification products or hybridization to an array—are communicated to a computer or processor, and the computer may execute software that, e.g., "counts" or "tallies" the frequency of occurrence of the various sequences of interest, compares frequencies, normalizes frequencies, performs quality control and/or statistical analysis, calculates fetal proportion or percentage of a maternal sample, calculates the dosage or frequency of genomic regions and/or chromosomes in view of the percent fetal nucleic acids, determines risk probabilities, or performs other calculations to determine chromosomal abnormalities. In one embodiment, the computer may comprise a personal computer, but the computer may comprise any type of machine that includes at least one processor and memory.

The output of the software component comprises a report with, e.g., a value of probability that a genomic region and/or a chromosome (such as, in this case, an X and/or Y chromosome) has a dosage abnormality. In some aspects this report is a value of the likelihood that a region or chromosome has two copies (e.g., is disomic) and a value of the likelihood that a region or chromosome has more copies (e.g., is trisomic) or less copies (e.g., is monosomic) copies. The report may be paper that is printed out, or electronic, which may be displayed on a monitor and/or communicated electronically to users via e-mail, FTP, text messaging, posted on a server, and the like. Although the normalization process of the invention is described as being implemented as software, it can also be implemented as a combination of hardware and software. In addition, software for normalization may be implemented as multiple components operating on the same or different computers. Both a server, if present, and the computer may include hardware components of typical computing devices (not shown), including a processor, input devices (e.g., keyboard, pointing device, microphone for voice commands, buttons, touchscreen, etc.), and output devices (e.g., a display device, speakers, and the like). The server and computer may include computer-readable media, e.g., memory and storage devices (e.g., flash memory, hard drive, optical disk drive, magnetic disk drive, and the like) containing computer instructions that implement the functionality disclosed when executed by the processor. The server and the computer may further include wired or wireless network communication interfaces for communication.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Preparation of DNA for Use in Tandem Ligation Procedures

Genomic DNA from subjects was obtained from Coriell Cell Repositories (Camden, N.J.) and fragmented by acoustic shearing (Covaris, Woburn, Mass.) to a mean fragment size of approximately 200 bp.

The DNA was biotinylated using standard procedures. Briefly, the Covaris fragmented DNA was end-repaired by generating the following reaction in a 1.5 ml microtube: 5 ug DNA, 12 µl 10×T4 ligase buffer (Enzymatics, Beverly Mass.), 50 U T4 polynucleotide kinase (Enzymatics, Beverly Mass.), and H20 to 120 µl. This was incubated at 37° C. for 30 minutes. The DNA was diluted using 10 mM Tris 1 mM EDTA pH 8.5 to desired final concentration of ~0.5 ng/µl.

5 µl DNA was placed in each well of a 96-well plate, and the plate sealed with an adhesive plate sealer and spun for 10 seconds at 250×g. The plate was then incubated at 95° C. for 3 minutes, and cooled to 25° C., and spun again for 10 seconds at 250×g. A biotinylation master mix was prepared in a 1.5 ml microtube to final concentration of: 1×TdT buffer (Enzymatics, Beverly Mass.), 8U TdT (Enzymatics, Beverly Mass.), 250 µM $CoCl_2$, 0.01 nmol/µl biotin-16-dUTP (Roche, Nutley N.J.), and H20 to 1.5 ml. 15 µl of the master mix was aliquoted into each well of a 96 well plate, and the plate sealed with adhesive plate sealer. The plate was spun for 10 seconds at 250×g and incubated for 37° C. for 60 minutes. Following incubation, the plate was spun again for 10 seconds at 250×g, and 7.5 µl precipitation mix (1 ng/µl Dextran Blue, 3 mM NaOAc) was added to each well.

The plate was sealed with an adhesive plate sealer and mixed using an IKA plate vortexer for 2 minutes at 3000 rpm. 27.5 µl of isopropanol was added into each well, the plate sealed with adhesive plate sealer, and vortexed for 5 minutes at 3000 rpm. The plate was spun for 20 minutes at 3000×g, the supernatant was decanted, and the plate inverted and centrifuged at 10×g for 1 minute onto an absorbent wipe. The plate was air-dried for 5 minutes, and the pellet resuspended in 10 µl 10 mM Tris pH8.0, 1 mM EDTA. An equimolar pool (40 nM each) of sets of first and second loci-specific fixed oligonucleotides was created from the oligos prepared as set forth above. A separate equimolar pool (20 µM each) of bridging oligonucleotides was likewise created for the assay processes based on the sequences of the selected genomic loci.

10 µg of strepavidin beads were transferred into the wells of a 96 well plate, and the supernatant was removed. 60 µl binding buffer (100 mM Tris pH 8.0, 10 mM EDTA, 500 mM $NaCl_2$, 58% formamide, 0.17% Tween-80), 10 µL 40 nM fixed sequence oligo pool and 30 µL of the biotinylated template DNA prepared in Example 2 were added to the beads. The plate was sealed with an adhesive plate sealer and vortexed at 3000 rpm until beads were resuspended. The oligos were annealed to the template DNA by incubation at 70° C. for 5 minutes, followed by slow cooling to 30° C.

The plate was placed on a raised bar magnetic plate for 2 minutes to pull the magnetic beads and associated DNA to the side of the wells. The supernatant was removed by pipetting, and was replaced with 50 µL of 60% binding buffer (v/v in water). The beads were resuspended by vortexing, placed on the magnet again, and the supernatant was removed. This bead wash procedure was repeated once using 50 uL 60% binding buffer, and repeated twice more using 50 µL wash buffer (10 mM Tris pH 8.0, 1 mM EDTA, 50 mM $NaCl_2$).

The beads were resuspended in 37 µl ligation reaction mix consisting of 1× Taq ligase buffer (Enzymatics, Beverly Mass.), 10U Taq ligase, and 2 uM bridging oligo pool (depending on the assay format), and incubated at 37° C. for one hour. Where appropriate, and depending on the assay format, a non-proofreading thermostable polymerase plus 200 nM each dNTP was included in this mixture. The plate was placed on a raised bar magnetic plate for 2 minutes to pull the magnetic beads and associated DNA to the side of the wells. The supernatant was removed by pipetting, and was replaced with 50 μL wash buffer. The beads were resuspended by vortexing, placed on the magnet again, and the supernatant was removed. The wash procedure was repeated once.

To elute the products from the strepavidin beads, 30 μl of 10 mM Tris 1 mM EDTA, pH 8.0 was added to each well of 96-well plate. The plate was sealed and mixed using an IKA vortexer for 2 minutes at 3000 rpm to resuspend the beads. The plate was incubated at 95° C. for 1 minute, and the supernatant aspirated using an 8-channel pipetter. 25 μl of supernatant from each well was transferred into a fresh 96-well plate for universal amplification.

Example 2

Universal Amplification of Ligated Products

The polymerized and/or ligated nucleic acids were amplified using universal PCR primers complementary to the universal sequences present in the first and second fixed sequence oligos hybridized to the nucleic acid regions of interest. 25 μl of each of the reaction mixtures of Example 3 were used in each amplification reaction. A 50 μL universal PCR reaction consisting of 25 μL eluted ligation product plus 1×Pfusion buffer (Finnzymes, Finland), 1M Betaine, 400 nM each dNTP, 1 U Pfusion error-correcting thermostable DNA polymerase, and primer pairs with sample tags used to uniquely identify individual samples prior to pooling and sequencing. The PCR was carried out under stringent conditions using a BioRad Tetrad™ thermocycler.

10 μl of universal PCR product from each of the samples were pooled and the pooled PCR product was purified and quantified using Quant-iT™ PicoGreen, (Invitrogen, Carlsbad, Calif.). The purified PCR products of were sequenced on a single lane of a slide on an Illumina HiSeq™ 2000. Sequencing runs typically give rise to ~100M raw reads, of which ~85M (85%) map to expected assay structures. This translated to an average of ~885K reads/sample across the experiment, and (in the case of an experiment using 96 loci) 9.2K reads/replicate/locus across 96 selected nucleic acid regions.

Example 3

Analysis of Polymorphic Loci to Assess Percent Fetal Contribution

To assess fetal nucleic acid proportion in the maternal samples, assays were designed against a set of SNP-containing loci on chromosomes 1 through 12, where two bridging oligos differing by one base were used to query each SNP (see, e.g., FIG. 3). SNPs were optimized for minor allele frequency in the HapMap 3 dataset. Duan, et al., Bioinformation, 3(3):139-41 (2008); Epub 2008 Nov. 9.

Oligonucleotides were synthesized by IDT (Coralville, Iowa) and pooled together to create a single multiplexed assay pool. PCR products were generated from each subject sample as previously described. Informative polymorphic loci were defined as loci where fetal alleles differed from maternal alleles. Because the assay exhibits allele specificities exceeding 99%, informative loci were readily identified when the fetal allele proportion of a locus was measured to be between 1 and 20%. A maximum likelihood was estimated using a binomial distribution, such as that described in co-pending application U.S. Ser. No. 13/553,012, filed 19 Jul. 2012, to determine the most likely fetal proportion based upon measurements from several informative loci. The results correlated well (R2>0.99) with the weighted average approach presented by Chu and colleagues (see, Chu, et al., Prenat. Diagn., 30:1226-29 (2010)).

Example 4

Detection of Y Chromosome Frequency Abnormalities Using Non-Polymorphic Sites in Chromosome-Specific Genomic Regions In a first embodiment, assays directed against specific genomic regions on the Y chromosome were used to identify the presence or absence of a Y chromosome frequency abnormality. The present assay system allowed the identification of the presence or absence of such an abnormality in the DNA of multiple individuals using a highly multiplexed system.

Multiple interrogations were prepared using oligonucleotides complementary to or derived from the Y chromosome (chrY), and chromosomes 13, 18 and 21 (chr13, chr18 and chr21). All oligonucleotides used in the tandem ligation formats were synthesized using conventional solid-phase chemistry. The oligos of the first fixed set and the bridging oligonucleotides were synthesized with 5' phosphate moieties to enable ligation to 3' hydroxyl termini of adjacent oligonucleotides. Thirty-two non-polymorphic assays were developed on chrY and compared to assays developed for chr13, chr18 and chr21 (see, e.g., Sparks, et al., Prenat. Diagn., 32(1):3-9 (2012) and Sparks, et al., Am J. Obstet. Gynecol. (2012), doi:10.1016/j.ajog.2012.01.030). Fetal fraction was measured using a set of SNP-containing loci on chromosomes 1 through 12 or chr13, chr18 and chr21. A fetal fraction estimate from these chromosomes was calculated using polymorphism detection and a probability algorithm as described in U.S. Ser. No. 13/316,154, filed 9 Dec. 2011 and Ser. No. 13/338,963, filed 28 Dec. 2011.

The fraction of Y chromosome counts was detected and computed to determine the PF_ChrY. The PF_ChrY was divided by the calculated PF_Poly. The result was subtracted from one to provide the YFF.

$$YFF = 1 - \left( \frac{PF\_Poly - PF\_ChrY}{PF\_Poly} \right)$$

The variance of the YFF was calculated in this instance by bootstrap sampling of Y assays counts, autosome assay counts and the calculated PF_Poly. Using models of 0 copies of Y, 1 copy of Y, and 2+ copies of Y, a Bayesian analysis was performed to estimate the probability of having 0, 1 or 2+ copies. One implementation used a truncated normal model for 0 copies, and normal distribution models for 1 or 2+ copies, using the standard deviations performed in the preceding step. When the difference is close to 0, the fetus is likely female, and when the difference is close to 1, the fetus is likely male. In the present example, when results for YFF was between 0.25 and 0.65 or beyond 3.5, the result was considered to be outside of reportable range; however, other thresholds derived from observations might be used to establish what is reportable.

Distributions of this fetal difference value were computed using bootstrap sampling, and a log 10 odds ratio was computed comparing the likelihood the difference is from a sample fitting the models of 0, 1, or 2+ chrY copies.

The results obtained show accuracy of the test for fetal sex was 100%, with 745 females correctly identified and 797 males correctly identified. A concordance of 99.8% between karyotyping and use of chrY analysis as described herein was achieved for fetal sex determination and determination of Y chromosomal aneuploidies. Table 1 shows the concordance of fetal Y chromosome status for the validation set.

| Karyotype Results | FYY Calculation Results | | | | |
|---|---|---|---|---|---|
| | Female (0) | Male (1) | Y Aneuploidy (2+) | No Result | Total |
| 46, XX (Female) | 274 | 0 | 0 | 9 | 283 |
| 45, X (Female) | 27 | 0 | 0 | 0 | 27 |
| 47, XXX (Female) | 1 | 0 | 0 | 0 | 1 |
| 46, XY (Male) | 0 | 193 | 0 | 10 | 203 |
| 47, XXY (Male) | 0 | 6 | 0 | 0 | 6 |
| 47, XYY (Male) | 0 | 1 | 2 | 0 | 3 |
| Total | 302 | 200 | 2 | 19 | 523 |

Example 5

Determination of Fetal XO, XX, XY, XXX, XXY, XYY and XXYY Genotypes

In order to allow analysis of fetal X chromosomes, sets of fixed sequence and bridging oligonucleotides were used as described to interrogate chromosome X loci in addition to the sets of oligonucleotides for interrogating the Y chromosome and chromosomes 13, 18 and 21. Computations to calculate the likelihood of the number of X chromosomes present in the fetus were added to computations calculating the likelihood of the number of chrY, chr13, chr18, and chr21, as well as determination of PF_Poly.

In this study, a set of 432 plasma samples were processed. All subjects were part of a blinded, case-control study, where all pregnant subjects had undergone invasive testing. The results obtained were compared to the karyotype obtained from invasive testing. All plasma samples from karyotyped pregnant individuals were processed according to the protocols detailed in Examples 1-4, supra. Sample acceptance criteria used to select samples were maternal age equal to or more than 18 years, gestational age equal to or more than 10 weeks, and singleton pregnancies. Egg donor pregnancies for both self- and genetically-unrelated egg donors were allowed.

First, the risk of T21, T18 and T13 for each sample was computed (see, e.g., U.S. Ser. No. 13/316,154, filed 9 Dec. 2011 and U.S. Ser. No. 13/338,963, filed 28 Dec. 2011). The risk scores were capped at 99% on the upper end and 0.01% on the lower end. A risk exceeding 1% classified a subject as a high risk for T21, T18 or T13. The concordance of the risk score-based classification for T21, T18 and T13 determined using the assays and the genetic status as determined by karyotype was identified.

Y chromosome analysis was performed as described in Example 4. For the X chromosome, the proportion of chrX vs. chr13, chr18 and chr21 counts was used. Models for 1, 2, or 3+ fetal copies of chrX were derived using the expected loss or gain based on measured PF_Poly in the sample.

The X fetal probability ($\hat{p}_1$) for a sample j was defined for fetal DNA comprising a single X chromosome as $$\hat{p}_1 = \frac{(1 - 0.5 * f_j) * p_0}{(1 - 0.5 * f_j) * p_0 + (1 - p_0)}$$

where $\hat{p}_1$ is the probability that the fetal DNA comprises a single X chromosome, $p_0$ is the reference proportion for a given chromosome and $f_j$ is the fetal fraction for the sample. The X fetal probability ($\hat{p}_2$) may be defined for fetal DNA comprising two X chromosomes as $$\hat{p}_2 = p_0$$

where $\hat{p}_2$ is the probability that the fetal DNA comprises two X chromosomes and $p_0$ is the reference proportion for a given chromosome. The X fetal probability ($\hat{p}_3$) for a sample j may be defined for fetal DNA comprising three X chromosomes as $$\hat{p}_3 = \frac{(1 + 0.5 * f_j) * p_0}{(1 + 0.5 * f_j) * p_0 + (1 - p_0)}$$

where $\hat{p}_3$ is the probability that the fetal DNA comprises three X chromosomes, $p_0$ is the reference proportion for a given chromosome and $f_j$ is the fetal fraction for the sample. The number of X chromosomes in the fetal DNA was then estimated by comparing the normalized probability value for each of $\hat{p}_1$, $\hat{p}_2$, and $\hat{p}_3$ which was calculated by dividing the probability values calculated above by the total sum of the probability values:

$$p1 = \frac{\hat{p}_1}{\hat{p}_1 + \hat{p}_2 + \hat{p}_3}, \quad p2 = \frac{\hat{p}_2}{\hat{p}_1 + \hat{p}_2 + \hat{p}_3}, \quad p3 = \frac{\hat{p}_3}{\hat{p}_1 + \hat{p}_2 + \hat{p}_3}$$

The highest normalized probability corresponded to the estimated number of X chromosomes in the fetal DNA.

Data acceptance criteria for determination of likelihood of the number of X chromosomes present in the fetus were essentially the same as that for the Y chromosome, except three computations are used to calculate the log 10 odds of a patient sample fitting the models for 1, 2, or 3+ fetal chromosome X copies, respectively: In combination with the computations performed for the number of fetal Y chromosomes, the test computing the likelihood of the number of X chromosomes present in the fetus used Bayesian models to evaluate the data from the X and Y chromosomes and compare hypotheses for the genotypes XO, XX, XY, XXX, XXY, XYY and XXYY. If the probability for a fetal sex (male versus female) was <99%, a "no result" for fetal X and Y chromosome status was generated. XFF represents roughly the number of fetal X chromosomes lost or gained.

414 of the 432 plasma samples passed the QC metrics for a sample pass rate of 95.8%. Results of T21, T18 and T13 gives ≥99% concordance with karyotyping, and the "no result" rate for reporting fetal chromosome X and Y status was <1%. The fetal X and Y chromosome analysis gave specificity for each sex chromosome aneuploidy (XO, XX, XY, XXX, XXY, XYY and XXYY) of ≥99%; for samples, gave sensitivity for the chromosome aneuploidy XO (which is associated with Turner Syndrome) of ≥80%; and the fetal X and Y chromosome analysis gave accuracy for fetal sex (male/female)>99%.

Using a risk score of 1% as the boundary for T21 versus non-T21 classification, a 100% concordance between the calculation of likelihood and karyotyping was observed; using a risk score of 1% as the boundary for T18 versus non-T18 classification, a 100% concordance between the calculation of likelihood and karyotyping was observed; and using a risk score of 1% as the boundary for T13 versus non-T13 classification, a 100% concordance between the calculation of likelihood and karyotyping was observed. The results for determination of fetal sex and aneuploidy are summarized in Table 2:

| Karyotype | XFF + YFF Calculation Results | | | | | | | | |
|---|---|---|---|---|---|---|---|---|---|
| | XX (Female) | XO (Female) | XXX (Female) | XY (Male) | XXY (Male) | XYY (Male) | XXYY (Male) | No Result | Total |
| 46, XX (Female) | 221 | 2 | 2 | 0 | 0 | 0 | 0 | 8 | 233 |
| 45, XO (Female) | 1 | 26 | 0 | 0 | 0 | 0 | 0 | 0 | 27 |
| 47, XXX (Female) | 0 | 0 | 1 | 0 | 0 | 0 | 0 | 0 | 1 |
| 46, XY (Male) | 0 | 0 | 0 | 155 | 0 | 0 | 0 | 10 | 165 |
| 47, XXY (Male) | 0 | 0 | 0 | 0 | 6 | 0 | 0 | 0 | 6 |
| Total | 222 | 28 | 3 | 155 | 6 | 0 | 0 | 18 | 432 |

The XFF+YFF test results gave a specificity for each XO and XXX aneuploidy sample of 99.5% (95% Wilson confidence interval 98.1-99.9) and a specificity for each XXY, XYY, and XXYY aneuploidy sample of 100% (95% Wilson confidence interval 99-100). The XFF+YFF test gave sensitivity for XO aneuploidy samples of 96.3% (95% Wilson confidence interval 82-99.8), which passes the acceptance criteria of ≥80%. The XFF+XYY test results gave accuracy for fetal sex of 100% (95% Wilson confidence interval 99-100).

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. A process to calculate a risk of X or Y chromosomal aneuploidy in a maternal blood, serum or plasma sample from a pregnant female comprising fetal and maternal nucleic acids, comprising the steps of:
   a) interrogating one or more Y chromosomal loci by hybridizing a first set of two or more sequence-specific oligonucleotide probes to twelve or more non-polymorphic loci, interrogating one or more X chromosomal loci by hybridizing a second set of two or more sequence-specific oligonucleotide probes to twelve or more non-polymorphic loci, and interrogating one or more loci on at least a first autosome by hybridizing a third set of two or more sequence-specific oligonucleotide probes to twelve or more non-polymorphic loci;
   b) ligating the hybridized first set of sequence-specific oligonucleotide probes, ligating the hybridized second set of sequence-specific oligonucleotide probes, and ligating the hybridized third set of sequence-specific oligonucleotide probes;
   c) amplifying the ligated first set of sequence-specific oligonucleotide probes, amplifying the ligated second set of sequence-specific oligonucleotide probes, and amplifying the ligated third set of sequence-specific oligonucleotide probes;
   d) generating, by a computer processor and based on the interrogating of the one or more Y chromosomal loci, the interrogating of the one or more X chromosomal loci, and the interrogating of the one or more loci on at least the first autosome, an estimation of a chromosome frequency for a Y chromosome, an X chromosome and the first autosome;
   e) calculating a fetal nucleic acid proportion in the maternal blood, serum or plasma sample by analyzing a frequency of polymorphisms on at least one autosome;
   f) calculating, by the computer processor, values of likelihood that the Y chromosome is present in no copies, one copy or two or more copies in the maternal blood, serum or plasma sample using the calculated fetal nucleic acid proportion;
   g) generating, by the computer processor, a calculated risk of aneuploidy of the Y chromosome in the maternal blood, serum or plasma sample by comparing the values of likelihood to a first mathematic model assuming no copies of the Y chromosome, a second mathematic model assuming one copy of the Y chromosome, and a third mathematic model assuming two or more copies of the Y chromosome;
   h) calculating, by the computer processor, values of likelihood that the X chromosome is present in one copy, two copies or three or more copies in the maternal blood, serum or plasma sample using the calculated fetal nucleic acid proportion; and
   i) generating, by the computer processor, a calculated risk of aneuploidy of the X chromosome in the maternal blood, serum or plasma sample by comparing the values of likelihood to a first mathematic model assuming one copy of the X chromosome, a second mathematic model assuming two copies of the X chromosome, and a third mathematic model assuming three or more copies of the X chromosome.

2. The process of claim 1, wherein the X or Y chromosomal aneuploidy is a fetal aneuploidy.

3. The process of claim 1, wherein at least ten or more polymorphic loci are interrogated.

4. The process of claim 3, wherein at ten or more polymorphic loci on at least two autosomes are interrogated.

5. The process of claim 4, wherein a fetal nucleic acid proportion in the maternal blood, serum or plasma sample is calculated by analyzing the frequency of polymorphisms from at least two autosomes.

6. The process of claim 4, wherein at least ten or more polymorphic loci on at least three autosomes are interrogated.

7. The process of claim 6, wherein the fetal nucleic acid proportion in the maternal blood, serum or plasma sample is calculated by analyzing the frequency of polymorphisms from at least three autosomes.

8. The process of claim 1, wherein at least 24 loci are interrogated on each of the X chromosome, the Y chromosome and the at least one autosome.

9. The process of claim 8, wherein at least 32 loci are interrogated on each of the X chromosome, the Y chromosome and the at least one autosome.

10. The process of claim 9, wherein each locus is measured at least 100 times.

11. The method of claim 1, wherein at least 96 polymorphic loci are measured to calculate the percent fetal nucleic acid proportion.

12. The process of claim 2, wherein the calculated risk of fetal aneuploidy is adjusted using extrinsic information on prior risk.

13. The process of claim 2, wherein a risk of X chromosome aneuploidy is calculated utilizing XFF.

14. The process of claim 2, wherein a risk of Y chromosome aneuploidy is calculated utilizing YFF.

15. The process of claim 1, wherein calculating the values of likelihood that the Y chromosome is present in no copies, one copy or two or more copies in the maternal blood, serum or plasma sample and calculating values of likelihood that the X chromosome is present in one copy, two copies or three or more copies in the maternal blood, serum or plasma sample is performed by bootstrap sampling.

16. The process of claim 1, wherein the calculating a risk step is performed using a log 10 odds ratio.

17. A process to calculate a risk of an X chromosomal aneuploidy in a maternal blood, serum or plasma sample comprising fetal and maternal nucleic acids, wherein the process steps are performed on a computer, comprising the steps of:
   a) interrogating one or more X chromosomal loci by hybridizing a first set of two or more sequence-specific oligonucleotide probes to twelve or more non-polymorphic loci;
   b) interrogating one or more polymorphic loci on at least a first autosome by hybridizing a second set of two or more sequence-specific oligonucleotide probes to twelve or more non-polymorphic loci;
   c) ligating the hybridized first set of sequence-specific oligonucleotide probes and ligating the hybridized second set of sequence-specific oligonucleotide probes;
   d) amplifying the ligated first set of sequence-specific oligonucleotide probes and amplifying the ligated second set of sequence-specific oligonucleotide probes;
   e) estimating a chromosome frequency for an X chromosome and the first autosome;
   f) calculating a fetal nucleic acid proportion in the maternal blood, serum or plasma sample by analyzing a frequency of polymorphic loci on at least one autosome;
   g) calculating values of likelihood that the X chromosome is present in one copy, two copies or more than two copies in the maternal blood, serum or plasma sample using the calculated fetal nucleic acid proportion; and
   h) calculating a risk of aneuploidy of the X chromosome in the maternal blood, serum or plasma sample by comparing the values of likelihood to a first mathematic model assuming one copy of the X chromosome, a second mathematic model assuming two copies of the X chromosome, and a third mathematic model assuming three copies of the X chromosome.

18. The process of claim 17, wherein the X chromosomal aneuploidy is a fetal aneuploidy.

19. The process of claim 18, further comprising determining whether the fetal nucleic acid proportion in the maternal blood, serum or plasma sample is adequate to reliably perform analysis.

20. The process of claim 17, wherein at least ten or more polymorphic loci are interrogated.

21. The process of claim 20, wherein at least ten or more polymorphic loci on at least two autosomes are interrogated.

22. The process of claim 21, wherein a fetal nucleic acid proportion in the maternal blood, serum or plasma sample is calculated by analyzing the frequency of polymorphic loci from at least two autosomes.

23. The process of claim 22, wherein at least ten or more polymorphic loci on at least three autosomes are interrogated.

24. The process of claim 23, wherein the fetal nucleic acid proportion in the maternal blood, serum or plasma sample is calculated by analyzing the frequency of polymorphisms from at least three autosomes.

25. The process of claim 17, wherein at least 24 loci are interrogated on the X chromosome.

26. The process of claim 25, wherein at least 32 loci are interrogated on each of the X chromosome and the at least one autosome.

27. The process of claim 25, wherein each locus is measured at least 20 times.

28. The method of claim 17, wherein at least 96 polymorphic loci are measured to calculate the fetal nucleic acid proportion.

29. The process of claim 18, wherein the calculated risk of fetal aneuploidy is adjusted using extrinsic information on prior risk.

30. The process of claim 18, wherein a risk of X chromosome aneuploidy is calculated utilizing XFF.

31. The process of claim 14, wherein the YFF calculation comprises a YFF value that is used to determine the presence of more than two copies of the Y chromosome in the fetal nucleic acid.

32. The process of claim 18, wherein the fetus does not have a Y chromosome when the YFF value is less than zero.

* * * * *